(12) United States Patent
Goforth et al.

(10) Patent No.: US 10,071,174 B2
(45) Date of Patent: Sep. 11, 2018

(54) BISMUTH PARTICLE X-RAY CONTRAST AGENTS

(75) Inventors: Andrea Goforth, Portland, OR (US); Anna Brown, Portland, OR (US)

(73) Assignee: Portland State University, Portland, OR (US)

( * ) Notice: Subject to any disclaimer, the term of this patent is extended or adjusted under 35 U.S.C. 154(b) by 1221 days.

(21) Appl. No.: 14/124,236

(22) PCT Filed: Jun. 6, 2012

(86) PCT No.: PCT/US2012/041147
§ 371 (c)(1),
(2), (4) Date: Mar. 13, 2014

(87) PCT Pub. No.: WO2012/170569
PCT Pub. Date: Dec. 13, 2012

(65) Prior Publication Data
US 2014/0194733 A1    Jul. 10, 2014

Related U.S. Application Data

(60) Provisional application No. 61/493,913, filed on Jun. 6, 2011.

(51) Int. Cl.
*A61K 49/04*    (2006.01)
*A61L 31/18*    (2006.01)
(Continued)

(52) U.S. Cl.
CPC .......... *A61K 49/0423* (2013.01); *A61B 90/39* (2016.02); *A61K 49/0414* (2013.01);
(Continued)

(58) Field of Classification Search
None
See application file for complete search history.

(56) References Cited

U.S. PATENT DOCUMENTS

| 5,725,517 A | 3/1998 | DeBusk |
| 6,198,807 B1 | 3/2001 | DeSena |

(Continued)

FOREIGN PATENT DOCUMENTS

| WO | WO 1994/019050 A1 | 9/1994 |
| WO | WO 96/16677 | 6/1996 |

(Continued)

OTHER PUBLICATIONS

Brown et al., "pH-Dependent Synthesis and Stability of Aqueous, Elemental Bismuth Glyconanoparticle Colloids: Potentially Biocompatible X-ray Contract Agents," *Chem. Matter.*, DOI: 10.1021/cm. 300083j (Apr. 10, 2012) (22 pages).

(Continued)

*Primary Examiner* — Robert A Wax
*Assistant Examiner* — Melissa S Mercier
(74) *Attorney, Agent, or Firm* — Klarquist Sparkman, LLP

(57) ABSTRACT

Radiopaque bismuth particles and methods of making and using the radiopaque bismuth particles are disclosed. The radiopaque bismuth particles include an elemental bismuth core and an outer coating comprising one or more coating agents. Disclosed radiopaque bismuth particles are suitable for use in surgical sponges and plastic objects.

11 Claims, 13 Drawing Sheets

(51) Int. Cl.
*C07F 9/94* (2006.01)
*B82Y 30/00* (2011.01)
*A61B 90/00* (2016.01)
*C08K 9/10* (2006.01)

(52) U.S. Cl.
CPC ............... *A61L 31/18* (2013.01); *B82Y 30/00* (2013.01); *C07F 9/94* (2013.01); *C08K 9/10* (2013.01); *Y10T 29/49826* (2015.01)

(56) References Cited

U.S. PATENT DOCUMENTS

| | | | |
|---|---|---|---|
| 6,818,199 | B1 | 11/2004 | Hainfeld et al. |
| 7,399,296 | B2 | 7/2008 | Poole et al. |
| 2004/0127824 | A1 | 7/2004 | Falahee |
| 2005/0049563 | A1 | 3/2005 | Fabian |
| 2005/0106119 | A1 | 5/2005 | Brandom et al. |
| 2007/0098640 | A1 | 5/2007 | Bonitatebus, Jr. et al. |
| 2007/0122620 | A1* | 5/2007 | Bonitatebus, Jr. ............ A61K 49/0423 428/403 |
| 2007/0219516 | A1 | 9/2007 | Patel et al. |
| 2009/0321689 | A1* | 12/2009 | Harada ............... B01F 17/0007 252/513 |

FOREIGN PATENT DOCUMENTS

| WO | WO 01/49340 A1 | 7/2001 |
|---|---|---|
| WO | WO 2003/075961 A2 | 9/2003 |
| WO | WO 2007/095454 A2 | 8/2007 |
| WO | WO 2009/049083 | 4/2009 |
| WO | WO 2010/066335 A1 | 6/2010 |

OTHER PUBLICATIONS

Fang et al., "Nanocrystalline bismuth synthesized via an in situ polymerization-microemulsion process," *Materials Letters*, 42:113-120 (2000).

Fang et al., "Self-assembled bismuth nanocrystallites," *Chem. Commun.*, pp. 1872-1873 (2001).

Fang et al., "Nanometer-sized Bismuth Crystallites Synthesized from a High-temperature Reducing System," *Mat. Res. Soc. Symp. Proc.*, vol. 676 pp. Y8.9.1-Y8.9.6 (2001).

International Search Report and Written Opinion dated Jul. 17, 2012, by Australian Patent Office for corresponding Application No. PCT/US2012/041147, filed Jun. 6, 2012 (11 pages).

Mohan, "Green bismuth," *Nature Chemistry*, 2:336 (Apr. 2010).

Shaw-Klein, "Material Selection When Printing Functional Traces on Medical Devices," *European Medical Device Technology* (May 1, 2010) (6 pages).

Wang et al., "Size- and Shape-Controlled Synthesis of Bismuth Naoparticles," *Chem. Mater.*, 20(11):3656-3662 (2008).

Yarema et al., "Highly Monodisperse Bismuth Nanoparticles and Their Three-Dimensional Superlattices," *J. Am. Chem. Soc.*, 132(43):15158-15159 (2010) (Abstract).

Extended European Search Report, dated Dec. 12, 2014, issued in corresponding European Patent Application No. 12796089.6 (6 pages).

First Office Action, dated Dec. 23, 2014, issued in corresponding China Patent Application No. 201280027876.4 (18 pages).

* cited by examiner

BISMUTH PARTICLE X-RAY CONTRAST AGENTS

CROSS REFERENCE TO RELATED APPLICATIONS

This is the U.S. National Stage of International Application No. PCT/US2012/041147, filed Jun. 6, 2012, which was published in English under PCT Article 21(2), which in turn claims the benefit of U.S. Provisional Application No. 61/493,913, filed Jun. 6, 2011, which is incorporated herein by reference in its entirety.

FIELD

This disclosure relates to radiopaque bismuth particles and methods of making and using the radiopaque bismuth particles.

BACKGROUND

Nanometer and micrometer sized particles are attractive X-ray contrast agents (XCAs) since they contain a large number of X-ray attenuating atoms in a small volume, which should allow use at low concentrations. Additionally the high contrast material will allow for attachment of biomolecules and/or ligands to the particle surface, potentially making highly specific site-directed contrast agents or variably miscible X-ray composite fillers (Cho et al., *T. in Molecular Medicine*, 2010, 16, 12, 561). Heavy element gold nanoparticles (AuNPs, Z=79) have begun to be explored as nano XCAs, primarily due to the ease of synthesis and morphological control that has been demonstrated for AuNPs over the last several decades (Popovtzer et al., *Nano Lett.* 2008, 8, 4593; Eck et al., *Nano Lett.* 2010, 10, 2318). However, gold is very expensive, making AuNPs a somewhat undesirable element for large scale systematic medical use. More importantly, while the oxidative stability of AuNPs infers a synthetic advantage in the laboratory, AuNPs larger than 5 nm pose a biological and environmental toxicity risk since they are not cleared by living organisms and are potentially bio-accumulating (Choi et al., *Nat. Biotechnology*, 2007, 25(10), 1165; Longmire et al. *Nanomedicine*, 2008, 3, 5, 703). Other X-ray opaque XCAs and fillers have included iopromide, barium sulfate, tin and lead, each with limitations, and not typically in particle form.

The recent popularity of green chemical techniques has put an emphasis on using water as a synthetic solvent, which can be problematic for metals prone to oxidation. Since any XCA used in a biological organism must have aqueous stability, desirable nanoparticles used as XCAs would be hydrolytically stable and have oxidative protection. The aqueous aerobic stabilization of nanomaterials, particularly those made of electropositive metals and semi-metals, has proven a challenge due to the difficulty in protecting against hydrolytic and oxidative decomposition. Gold has become a model system for the study of nanoparticle formation, stability, and growth mechanisms, in part due to the oxidative inertness of this element. However, most metals are susceptible to the formation of oxides on their surface, which can lead to the eventual oxidative degradation of the material, as in iron, or to protection of the metal, as in aluminum. This makes the stabilization of aqueous metal nanomaterials difficult, as a nanosize particle inherently has a high surface area to volume ratio. The high surface area imparts a variety of unique and desirable properties; however, for non-oxidatively inert elements, the high surface area can pose stability challenges in an aqueous or aerobic environment. In non-polar environments, similar challenges present in stabilizing the high-energy particle surfaces against aggregation.

SUMMARY

Disclosed herein are embodiments of radiopaque bismuth particles having an inner core comprising elemental bismuth and an outer coating. Applying an outer coating to a bismuth core provides a particle with tunable surface characteristics, thereby facilitating homogeneous dispersion in a liquid or solid matrix to achieve highly X-ray attenuating dispersions and composites for applications, including biomedical X-ray contrast agents, X-ray opaque inks, X-ray opaque surgical plastics and sponges, and X-ray opaque toys, among others.

In some embodiments, the particles have an average diameter of up to 1 mm. In certain embodiments, the particles are microparticles, nanoparticles, or a combination thereof. The outer coating may substantially continuous or discontinuous, and may be associated with the core by chemical bonding (i.e., ionic, covalent, or coordinate bonding) or by electrostatic interactions (e.g., van der Waals forces and/or adsorption of electron-dense solvents on electron-poor metal surfaces). In some embodiments, the coating comprises one or more hydrophilic, hydrophobic, or amphiphilic coating, or capping, agents. The coating agents are selected to provide the particles with desirable surface functionalities and properties. Suitable coating agents include alcohols, aliphatic compounds (e.g., alkanes, alkenes, alkynes), alkylquinolinium cations, amines, aryl compounds (e.g., a phenyl-substituted alkene), carbohydrates (e.g., monosaccharides, disaccharides, and polysaccharides), carboxylic acids, ketones, aldehydes, thiocarboxylic acids, organothiols (e.g., aliphatic thiols, such as alkanethiols), polymers (e.g., polymers comprising monomers having a polymerizable alkene group, such as polyacrylic acid, polystyrene or polyvinylpyrrolidone), perhalogenated alkyl phosphonates (e.g., a perfluorinated alkyl phosphonate), perhalogenated alkyl siloxanes (e.g., a perfluorinated alkyl siloxane) and combinations thereof.

In some embodiments, the coating agents stabilize the nanoparticle against oxidative degradation, e.g., in aqueous environments. In other embodiments, the coating agents provide the particles with hydrophobic characteristics, which provide stable colloidal dispersions in non-polar solvents. In still other embodiments, the coating agents provide the nanoparticles with a positively or negatively charged surface. The coating agents also may prevent or minimize particle aggregation.

Embodiments of the disclosed bismuth particles are prepared by a "top-down" synthesis or a "bottom-up" synthesis. Embodiments of the top-down synthesis include (a) combining bismuth and at least one coating agent to produce a mixture; (b) subjecting the mixture to mechanical mixing comprising ball-milling, grinding, or a combination thereof, wherein the mechanical mixing is sufficient to break apart at least a portion of the bismuth to form bismuth microparticles, bismuth nanoparticles, or a combination thereof, whereby the at least one coating agent covalently binds, ionically binds, or adsorbs to outer surfaces of the bismuth microparticles, bismuth nanoparticles, or combination thereof to form coated bismuth particles; and (c) isolating coated bismuth particles from the mixture. Isolating coated bismuth particles may include extracting at least some of the coated bismuth particles from the mixture with a solvent, and recovering coated bismuth particles by removing the solvent.

Embodiments of the bottom-up synthesis include (a) at least partially solubilizing a bismuth salt in a solution comprising a solvent and at least one coating agent to form a solubilized bismuth solution; (b) adding a reducing agent to the solubilized bismuth solution to reduce bismuth ions and form elemental bismuth particles, whereby the at least one coating agent forms an outer coating on the elemental bismuth particles to form radiopaque coated bismuth particles comprising an elemental bismuth core and an outer coating comprising the coating agent; and (c) isolating coated bismuth particles from the mixture. Isolating coated bismuth particles may include recovering the radiopaque coated bismuth particles from the solution via centrifugation, filtration, extraction into a non-polar solvent, precipitation, or a combination thereof. Suitable bismuth salts include bismuth nitrate pentahydrate, bismuth boride, bismuth chloride, bismuth iodide, bismuth acetate, bismuth citrate, bismuth oxide, or a combination thereof. Suitable reducing agents include sodium borohydride, triethylene tetramine, borane trimethyltetramine, borane morpholine, a polyol, an aliphatic amine, or a combination thereof. In one embodiment, the coating agent comprises a functional group capable of imparting a positive charge or a negative charge to the outer coating. In another embodiment, the coating agent is amphiphilic, and the coated bismuth particles are hydrophobic.

In some embodiments, a radiopaque polymeric composition includes a polymeric matrix and a plurality of bismuth particles dispersed within the polymeric matrix. At least some of the bismuth particles comprise an elemental bismuth core and an outer coating agent as described above. In one embodiment, the outer coating is substantially continuous. The particles may be microparticles, nanoparticles, or a combination thereof.

In one embodiment, a radiopaque surgical sponge includes a radiopaque member comprising the radiopaque polymeric composition. The radiopaque member may be, e.g., a string (such as a cotton or acrylic fiber string) or a disk. In one embodiment, at least a portion of the radiopaque member is securely attached to a surface of the sponge. In another embodiment, the radiopaque member is embedded in the sponge. In some embodiments, the bismuth particles are coated with hexane, 1-pentene, oleic acid, or a combination thereof. In one embodiment, the coated bismuth particles are dispersed in a silicone matrix, and the radiopaque member is impregnated with or coated with the polymeric composition. In one embodiment, the mass ratio of bismuth:silicone is 0.5 to 20.

In another embodiment, at least a portion of a plastic object includes the radiopaque polymeric composition. The portion has a sufficient size and a sufficient concentration of bismuth particles to enable X-ray visualization of the plastic object. In one embodiment, substantially all of the plastic object comprises the radiopaque polymeric composition. In certain embodiments, the polymeric matrix is polypropylene, poly(methylmethacrylate), polyethylene, poly(tetrafluoroethylene), polystyrene, polyethylene terephthalate, polyurethane, or a combination thereof. In some embodiments, radiopaque bismuth particles are incorporated into a plastic object by combining the radiopaque coated bismuth particles, or a polymeric composition comprising the radiopaque coated bismuth particles, (1) with molten plastic, (2) with plastic pellets and subsequently melting the plastic pellets, or (3) with monomers and subsequently polymerizing the monomers to form a plastic.

In still another embodiment, a radiopaque ink includes the radiopaque polymeric composition. In some embodiments, the bismuth particles are coated with a carbohydrate or phenyl-substituted alkene. The polymeric matrix may be, e.g., dextran or polystyrene.

In another embodiment, a radiopaque tag or label includes the radiopaque polymeric composition. In one embodiment, the tag consists essentially of the radiopaque polymeric composition. In another embodiment, the radiopaque polymeric composition is applied as a coating to a tag substrate, such as a paper-based or plastic tag. The radiopaque tag may further include an adhesive capable of forming a permanent bond or a temporary, removable bond to an object.

Embodiments of a radiopaque ink include a solvent and a plurality of bismuth particles. At least some of the bismuth particles comprise an elemental bismuth core and an outer coating agent as described above. The coating agent may be an alkene, a carbohydrate, an alkanethiol, a thiocarboxylate, an aliphatic amine, polyacrylic acid, polyvinylpyrrolidone, or a combination thereof.

The foregoing and other objects, features, and advantages of the invention will become more apparent from the following detailed description, which proceeds with reference to the accompanying figures.

DETAILED DESCRIPTION

Figure 1:
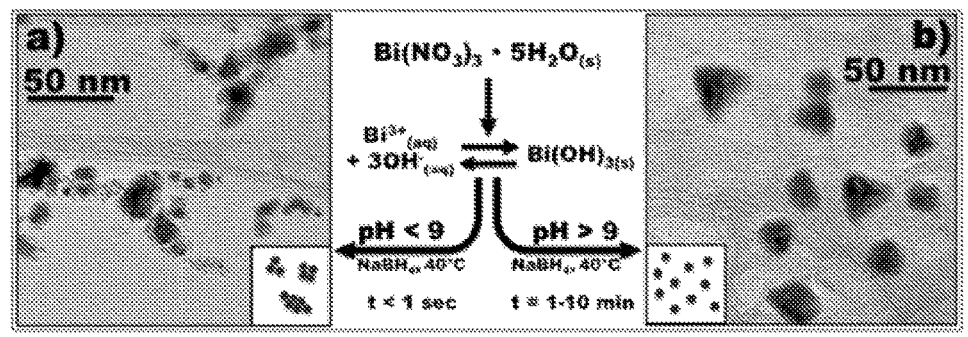
FIG. 1 is a scheme illustrating pH-dependent synthesis of colloidally stable bismuth(0) glyconanoparticles, and transmission electron microscopy photographs of the particles prepared at pH<9 (a) and pH>9 (b).
Figure 2:
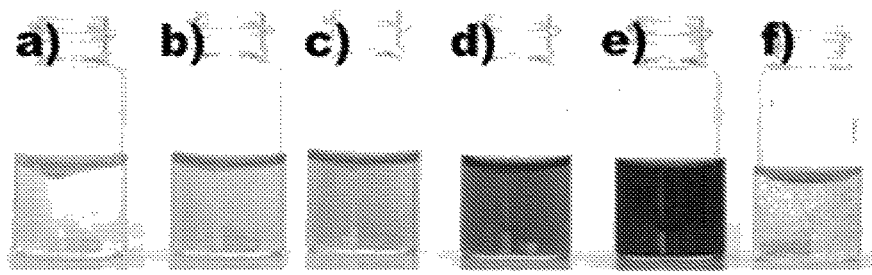
FIGS. 2a-2f are photographs illustrating the synthesis of dextran-coated bismuth nanoparticles in aqueous solution as a function of time. A colorless solution or white suspension of bismuth nitrate in the presence of glycine and dextran (FIG. 2a) is treated with a reducing agent, leading to development (FIGS. 2b-2e) of a black colloidal suspension of bismuth nanoparticles (FIG. 2e). Particle synthesis in the absence of dextran or at pH<8 produced unstable aggregates (FIG. 2f).

Bismuth is an attractive element for a nanomaterial or micromaterial XCA due to its high atomic number (Z=83) and well-known biological tolerance (Briand et al., *Chem. Rev.* 1999, 99, 2601). The high atomic number, coupled with the high density of the solid, makes bismuth-based contrast agents more X-ray opaque on a per atom basis than current, clinically used molecular iodine-based (Z=53) contrast agents, particulate barium-based (Z=56) contrast agents and fillers/additives, and tin- or lead-based (Z=50 and 82, respectively) shielding agents and X-ray opaque additives. Additionally, the high biological tolerance for bismuth, especially compared to most heavy metals (e.g., lead, thallium, and even gold), should allow for safe medical use during imaging and biological clearance after imaging. Furthermore, bismuth is twice as abundant as gold and much less expensive; gold currently is about two thousand times more expensive than bismuth. Bismuth is also less expensive and less toxic than lead or tin.

Medically, bismuth(III) chelate solutions have been used for centuries in relatively high doses (multiple gram doses per day) as safe anti-microbial and anti-emesis treatments with minimal known toxicity, despite the fact that these preparations have been predominantly chemically ill-defined. Bismuth(III) complexes present in blood are thought to be cleared by urinary excretion via metallothionine, a cysteine rich protein abundant in the kidneys that has been shown to have preferential affinity for bismuth over other metals, regardless of pH (Sun et al., *J. Bio. Chem,* 1999, 274, 41, 29094).

However, elemental BiNPs readily undergo oxidation and hydrolysis in water, rendering them difficult to synthesize and stabilize in an aqueous environment while simultaneously making them more likely to decompose to small, benign molecular or ionic Bi(III) species in vivo when used as intravenously injectable XCAs. While the hydrolytic instability of BiNPs may prove advantageous for a medical application, synthesis and stability of aqueous BiNP colloids is a substantial hurdle, as is stabilization of aqueous BiNP colloids for a time period suitable as an imaging window (e.g., up to 24 hours) (Brown et al., *Chem. Mater.,* 10 Apr. 2012, DOI: 10.1021/cm300083j). The majority of BiNP preparations reported to date are carried out anaerobically using organic solvents and morphology-controlling surfactants of poor or unknown biocompatibility. These syntheses yield hydrophobic BiNPs, or present challenges for purification from excess, potentially toxic reagents prior to a biological application. To date a synthesis method that yields small (i.e., <20 nm), hydrophilic, hydrolytically stable BiNPs suitable for use as intravenously injectable XCAs has not been reported.

Disclosed herein are methods for synthesizing stable, surface-tailored elemental bismuth microparticles and nanoparticles as tunably miscible, highly X-ray-attenuating liquid- or solid-phase dispersants, and applications for using the bismuth particles. In some embodiments, the bismuth particles are prepared with highly biocompatible reagents. Methods for synthesizing and using coated bismuth particles also are disclosed. Embodiments of the disclosed particles have an outer coating, which provides tunability of surface properties and facilitates integration in and compatibility with desired matrices, such as liquids and plastics. Embodiments of the disclosed particles are small, very dense, and radiopaque.

I. Terms and Definitions

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of ingredients, properties such as molecular weight, percentages, and so forth, as used in the specification or claims are to be understood as being modified by the term "about." Unless otherwise indicated, non-numerical properties such as amorphous, crystalline, homogeneous, and so forth as used in the specification or claims are to be understood as being modified by the term "substantially," meaning to a great extent or degree. Accordingly, unless otherwise indicated, implicitly or explicitly, the numerical parameters and/or non-numerical properties set forth are approximations that may depend on the desired properties sought, limits of detection under standard test conditions/methods, limitations of the processing method, and/or the nature of the parameter or property. When directly and explicitly distinguishing embodiments from discussed prior art, the embodiment numbers are not approximates unless the word "about" is recited.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2).

In order to facilitate review of the various embodiments of the disclosure, the following explanations of specific terms are provided:

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group). Exemplary aliphatic substituents include, for instance, amine, amide, sulfonamide, halogen, cyano, carboxy, hydroxy, mercapto, trifluoromethyl, alkyl, alkoxy, alkylthio, thioalkoxy, arylalkyl, heteroaryl, alkylamino, dialkylamino, or other functionality.

Alkyl refers to a hydrocarbon group having a saturated carbon chain. The chain may be cyclic, branched or unbranched. The term lower alkyl means the chain includes 1-10 carbon atoms. The terms alkenyl and alkynyl refer to hydrocarbon groups having carbon chains containing one or more double or triple bonds, respectively. Unless expressly referred to as unsubstituted, an alkyl group can either be unsubstituted or substituted.

Alkylquinolinium refers to a heterocyclic aromatic cation having the general formula $C_9H_5NR$:

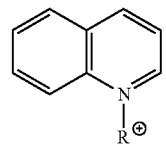

where R is alkyl.

Aromatic or aryl compounds are unsaturated, cyclic hydrocarbons having alternate single and double bonds. Benzene, a 6-carbon ring containing three double bonds, is a typical aromatic compound. Unless expressly referred to as unsubstituted, an aryl compound can either be unsubstituted or substituted.

Carbohydrate: An organic compound that consists only of carbon, hydrogen, and oxygen, usually with a hydrogen:oxygen atom ratio of 2:1. Carbohydrates include monosaccharides, disaccharides, and polysaccharides. Monosaccharides are aldehydes or ketones with two or more hydroxyl groups, and a general chemical formula of $C_nH_{2n}O_n$. Disaccharides are formed from two monosaccharides linked together by a glycosidic bond. A polysaccharide is a polymer of monosaccharides linked together by glycosidic bonds.

Ligand: As used herein, a ligand is a molecule or ion that is capable of attaching to a metal atom by coordinate bonding.

Microparticle: A microscale particle with a size that is measured in microns, for example, a microscopic particle (microparticle) that has at least one dimension of less than 1 mm.

Nanoparticle (NP): A nanoscale particle with a size that is measured in nanometers, for example, a nanoscopic particle that has at least one dimension of less than about 1 μm. Examples of nanoparticles include paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoprisms, nanoropes and quantum dots. A nanoparticle can produce a detectable signal, for example, through absorption and/or emission of photons (including radio frequency and visible photons) and plasmon resonance.

Organothiol: An organic compound containing a thiol (—SH) group.

Phosphonate: An organic compound containing R—PO(OH)$_2$, R—PO(OH)(OR) or R—PO(OR)$_2$ groups where each R individually is alkyl or aryl.

Plastic: As used herein, a plastic is material comprising a high molecular weight polymer, usually synthetic, and typically combined with other components, such as curatives, fillers, reinforcing agents, colorants, plasticizers, etc. The mixture can be formed or molded under heat and pressure in its raw state. Plastics may be shaped by compression molding or injection molding. The term plastic also includes thermoset polymers, which are liquid or malleable prepolymers that can be irreversibly cured through heat, chemical reaction, or irradiation to form a plastic. Plastics may be flexible or rigid. Rigid plastics may be machined. Exemplary plastics include, but are not limited to, polyethylene, polypropylene, acrylic polymers, polystyrene, cellulosics, nylons, fluorocarbon resins, phenolics, polycarbonates, ABS resins, polyvinyl chloride, polytetrafluoroethylene, and polybutylene terephthalate.

Powder: A composition comprising dispersed solid particles that are relatively free flowing from one another.

Siloxane: A chemical compound comprising one or more units of $R_2SiO_2$ where R is hydrogen or a hydrocarbon group. Siloxanes may include a branched or unbranched backbone of alternating silicon and oxygen atoms with side chains, R, attached to the silicon atoms.

Substituted: A fundamental compound, such as an aryl or aliphatic compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a hydrocarbon chain may have a substituent bonded thereto, such as one or more halogens, an aryl group, a cyclic group, a heteroaryl group or a heterocyclic group.

Thiocarboxylic acid: A carboxylic acid in which one or both oxygen atoms are replaced with sulfur, e.g., RC(O)SH, RC(S)OH, or RC(S)SH, where R is an aliphatic or aryl group. A thiocarboxylate is the corresponding anion of a thiocarboxylic acid.

XCA: X-ray contrast agent.

II. Bismuth Particles

Embodiments of bismuth particles are disclosed. The disclosed bismuth particles are suitable for incorporation into a variety of matrices, or host materials, while maintaining the structural integrity or health of the host material. Some embodiments of the disclosed bismuth particles are colloidally stable (in solution), minimally structurally damaging (in a solid composite), and/or well dispersed in a desired host matrix (solution or solid composite) while being highly visible by X-ray imaging.

The particles are suitable for use in applications where the presence of a radiopaque and/or visibly colored component is desirable. Bismuth's high atomic number (Z=83) provides superior X-ray attenuation. Bismuth particles can be prepared to include 100s-1000s of atoms in a small volume (e.g., $nm^3$-$\mu m^3$). The high atomic number makes bismuth-based contrast agents more X-ray opaque on a per-atom basis than lower atomic number elements, such as iodine (Z=53). Bismuth nanoparticles and microparticles also have a high surface area to volume ratio, which facilitates coating the particles with small-molecules to selectively control the surface functionality and/or polarity.

The particle surface can be tuned, or altered, via bonded and/or adsorbed surface coating, or capping, agents to provide characteristics (e.g., hydrophobicity) suitable for desired applications. Suitable coating agents include, e.g., solvents, polymers, and ligands. The coating agent may be associated with the bismuth core by chemical bonding (e.g., ionic bonding, covalent bonding, or coordinate bonding) or by electrostatic interactions (e.g., van der Waals forces). In some embodiments, the disclosed particles are microparticles, nanoparticles, or a combination thereof.

In the disclosed embodiments, the bismuth particles have an inner core comprising elemental bismuth and an outer coating comprising one or more coating agents. The outer coating may be substantially continuous or discontinuous. The coating agents are used to tune the surface functionality and properties of the particles. The coating agents may be hydrophilic, hydrophobic, or amphiphilic. In some embodiments, the outer coating comprises one or more coating agents that stabilize the nanoparticle against oxidative degradation, e.g., in aqueous environments. In other embodiments, the outer coating comprises one or more coating agents that increase the hydrophobicity of the particle, rendering the particle compatible with a hydrophobic matrix. In certain embodiments, the particles include coating agents that impart a charge to the particle surface, thereby providing the particle with a positively- or negatively-charged surface. In some embodiments, the coating agents also may prevent or minimize particle aggregation.

In some embodiments, bismuth particles are synthesized in aqueous solution in the presence of a carbohydrate (i.e., $C_x(H_2O)_y$, where x and y are integers), such as dextran, thereby forming a dextran and water coating around the particle. Transmission electron microscopy, line diffraction spacing, and powder X-ray diffraction indicate that the particles have crystalline, rhombohedral bismuth cores. In certain embodiments, the glycoparticles (i.e., dextran/water-coated particles) are nanoparticles with a hydrodynamic diameter of less than 150 nm, less than 100 nm, 10 nm to 150 nm, or 10 nm to 125 nm, such as 30 nm to 120 nm, 20 nm to 110 nm, or 10 nm to 100 nm. In certain embodiments, the nanoparticles may have an average hydrodynamic diameter of 50-75 nm, including a crystallite bismuth inner core having an average diameter of 15-25 nm and an outer surfactant and water coating. At pH values ranging from 7.4-10, the coating appears to impart colloidal stability to the glycoparticles and provide reasonably long-term protection against hydrolysis (FIGS. 9a-c). In some examples, dextran-coated bismuth nanoparticles were colloidally stable and did not aggregate or decompose to oxidized products (e.g., bismuth(III) solids, such as $Bi(OH)_3$ or $Bi_2O_3$, or bismuth (III) solution species, such as $BiO_2^-$ or $BiO_3^{3-}$) for periods as long as 12 months when stored in aqueous solution.

In some embodiments, bismuth particles are synthesized in the presence of small molecules that provide a surface charge to the particles, thereby providing hydrophilic, or polar, particles. For example, Tris (tris(hydroxymethyl) amino-methane) imparts a positive charge from the amine group, whereas tricine ((N-2-hydroxy-1,1-bis(hydroxymethyl)ethyl)glycine) has a carboxylic acid group and imparts a negative charge. Bismuth particles having a surface charge may be incorporated into polar matrices, including, but not limited to, aqueous media such as water or water-soluble inks, lower alkyl alcohols, dextran, poly(methyl methacrylate), and poly(ethylene glycol).

In certain applications, hydrophobic particles are desirable. To render the particles hydrophobic, synthesis can be performed in the presence of a surfactant or amphiphilic coating agent (e.g., a ligand) comprising a hydrophobic moiety and a hydrophilic moiety. The hydrophilic moiety will interact with the bismuth particle surface, and the hydrophobic moiety will protrude into the surrounding solution, thereby making the particles compatible with a hydrophobic, or non-polar, matrix. Alternatively, bismuth particle synthesis can be performed in a non-polar solvent or solution. Non-polar solvent and/or solute molecules may act as the coating agent(s). Suitable non-polar matrices include medical polymers (e.g., certain silicones), oils (e.g., linseed oil, mineral oil), waxes (e.g., wax-based inks), non-polar solvents such as toluene, and plastics (e.g., polyethylene, polypropylene, polystyrene).

Suitable coating agents include, e.g., alcohols, aliphatic compounds (e.g., alkanes, alkenes, alkynes), alkylquinolinium cations, amines, aryl compounds (e.g., a phenyl-substituted alkene), carbohydrates (e.g., monosaccharides, disaccharides, and polysaccharides), carboxylic acids, ketones, aldehydes, thiocarboxylic acids, organothiols (e.g., aliphatic thiols, such as alkanethiols), polymers (e.g., polymers comprising monomers having a polymerizable alkene group, such as polyacrylic acid, polystyrene or polyvinylpyrrolidone), perhalogenated alkyl phosphonates (e.g., a perfluorinated alkyl phosphonate), perhalogenated alkyl siloxanes (e.g., a perfluorinated alkyl siloxane) or a combination thereof. In some embodiments, the coating agent is selected from $C_nH_{2n}O_n$ where n is from 3 to 20, substituted or unsubstituted $C_{1-20}$ aliphatic, substituted or unsubstituted $C_{5-10}$ cycloalkyl or heterocycloalkyl, substituted or unsubstituted $C_{5-10}$ aryl or heteroaryl, ROH, RSH, $RNH_2$, $R_2CO$, RCOOH, RC(O)SH, RC(S)OH, RC(S)SH, or $C_9H_5NR$ where each R independently is a substituted or unsubstituted aliphatic, cycloalkyl, cycloheteroalkyl, or aryl group. In certain embodiments, R is an alkyl group, such as a $C_1$-$C_{20}$ alkyl group or a lower alkyl group (e.g., $C_1$-$C_{10}$ alkyl). In other embodiments, R is an alkenyl group, such as a $C_2$-$C_{20}$ alkenyl group. Exemplary coating agents include, but are not limited to, acetone, 1-decene, dihydroxyacetone, ethanol, ethanolamine, fructose, glucose, hexanes, maltose, mannose, octanol, octyl amine, oleic acid, oleylamine, oxaloacetic acid, 1-pentene, polyacrylic acid, polyvinylpyrrolidone, styrene, and combinations thereof.

In some examples, octanol, octylamine, oleylamine, oleic acid, and/or 1-pentene were utilized as coating agents to prepare hydrophobic bismuth particles. Bismuth particles coated with a non-polar coating agent (such as an alkane, and alkene, or an aryl compound), can be mixed with a non-polar matrix (e.g., certain silicones, polypropylene, polystyrene, polytetrafluoroethylene (PTFE), an oil, or a wax) to produce bismuth particles embedded within a support matrix or a colloidal suspension of bismuth particles in a non-polar solvent. In some examples, bismuth particles were coated with hexanes, hexanes and oleic acid, or 1-pentene, and embedded within a silicone support matrix.

In some examples, dihydroxyacetone, glucose, and/or dextran were utilized as coating agents to prepare hydrophilic bismuth particles. Bismuth particles coated with a hydrophilic coating agent can be mixed with a polar matrix (e.g., aqueous solutions, glycerol, certain silicones, polyurethanes) to produce bismuth particles embedded within a support matrix or colloidal suspensions of bismuth particles in a polar solvent.

III. Particle Synthesis

Embodiments of the disclosed microparticles and nanoparticles can be synthesized by various methods. In some embodiments, a bismuth salt is dissolved in a suitable solvent and reduced to form bismuth nanoparticles with an outer coating comprising the solvent. In certain embodiments, the solution further includes an additional coating agent, and bismuth nanoparticles with an outer coating comprising solvent and the additional coating agent are formed. In other embodiments, bismuth powder may be mechanically mixed (e.g., by ball milling) with a coating agent, whereby the coating agent adsorbs or binds to the particle surfaces, forming coated bismuth microparticles and/or nanoparticles.

In some embodiments, an aerobic, aqueous solution method is used to prepare chemically and colloidally stable, water-soluble, and potentially biocompatible bismuth nanoparticles. The aerobic, aqueous solution method has several advantages over existing BiNP preparations: 1) no phase transfer steps post-synthesis are needed; 2) simplified preparation and purification with highly biocompatible starting materials; and/or 3) reduced overall environmental impact.

A. Reduction of Bismuth Cations in a Solvent with One or More Coating Agent(s)

The synthesis of small nanomaterials from metal cations often requires a strong reducing agent and controlled kinetics to avoid formation of bulk materials, and to promote uniform growth (Warren et al. *J. Am. Chem. Soc.* 2007, 129, 10072). Disclosed herein are embodiments of a method that takes advantage of a bismuth oxide complex that forms in aqueous solutions, and pH control thereof, to kinetically slow the formation of bismuth nanoparticles and allow sufficiently slow growth such that particles can be individually coated and oxidatively stabilized. Embodiments of the disclosed method advantageously include fewer purification steps from solvent and surfactant.

In some embodiments, bismuth cations are reduced in the presence of a solvent and one or more coating, or capping, agents to form elemental bismuth nanoparticles having an outer coating comprising molecules of the coating agent. In certain embodiments, the outer coating further includes solvent molecules. These syntheses are also referred to as "bottom-up" syntheses since atoms are added to growing particles.

In one example, bismuth nitrate, $Bi(NO_3)_3.5H_2O$ is solubilized by aqueous potassium hydroxide to form $Bi(OH)_3.3H_2O_{(aq)}$. Sodium borohydride then reduces $Bi^{3+}$ to $Bi^0$. Bismuth nitrate pentahydrate is an inexpensive, readily available, and easily dissolved (at low pH, or in dilute aqueous solutions) bismuth(III) source. Sodium borohydride decomposes in aqueous solution to produce a gaseous product ($H_2$) and a soluble sodium salt (e.g., $NaBiO_2$) that can be removed by dialysis.

In aqueous solution, the bismuth cation $Bi^{3+}$ is known to form a highly acidic aquo-cation with a pKa of approximately 1.1 in dilute solution. In concentrated solutions, or upon titration with a base, aqueous Bi(III) is expected to form an insoluble basic salt in pH-dependent equilibrium with a soluble bismuth(III) species. The fully hydrated cation, $[Bi(OH_2)_6]^{3+}$, can lose up to 3 protons to yield the sparingly soluble, neutral species $Bi(OH)_3(OH_2)_3$, which can continue to hydrolyze to the insoluble $Bi_2O_3$. The aqueous solution form of the bismuth-oxo-cation is also dictated by the identity of the counterion. For example, bismuth oxychloride will be formed when bismuth chloride is hydrolyzed. $Bi^{3+}$ solutions at high pH (e.g., pH greater than or equal to 9) include several large, rather exotic, hydrolyzed bismuth polyanions, (e.g., $Bi_4O_7$ and $[Bi_6O_6]^{6+}$) or sparingly soluble sub-oxides (e.g., bismuth sub nitrate $BiO(NO_3)$. Bismuth (III) nitrate pentahydrate, the $Bi^{3+}$ source of bismuth used in Example 1, is reported to decompose in water and precipitate at high pH to $BiO(NO_3)$ or $Bi_2O_3$. The predominant species of bismuth in aerated water is an oxidized solid over most of the pH range. The onset of precipitation in a dilute solution (e.g., 2.4 mM) occurs at approximately pH 4, and prior to the addition of three molar equivalents of hydroxide.

Titration data for bismuth nitrate pentahydrate shows that the aqueous solution of $Bi(NO_3)_3$ is moderately acidic with an initial pH of slightly less than 2. Qualitatively the solution becomes clear at low concentration and with sonication, suggesting complete dissolution of the bismuth nitrate pentahydrate. The titration curve is indicative of a weak acid with an equivalence point between 2 and 3 molar equivalences of KOH, which is coupled with a visible formation of a solid precipitate. The complex interplay between Bi(III) solution species equilibria, which involves species whose identities and solubilities are pH dependent, suggests that controlling the pH of the aqueous reaction will provide a measure of kinetic control for formation of elemental bismuth nanoparticles.

A mechanism consistent with the observed behavior is shown in Scheme 1 (FIG. 1). For simplicity, one can assume that a suspension of solid bismuth hydroxide is in equilibrium with aqueous bismuth(III) and hydroxide ions, and that the equilibrium is dependent on pH, with a decreased bismuth(III) concentration achieved by increasing pH according to LeChatelier's principle. This equilibrium is the overall rate-limiting reaction for the formation of elemental bismuth particles. Bismuth particle formation is rate limited by interaction between a reducing agent (e.g., sodium borohydride) and free bismuth ions. When the soluble bismuth (III) precursor is depleted by reaction with a reducing agent to form bismuth(0) nanoparticles, the solid equilibrium shifts to replenish the solution precursor at the expense of the precipitate. Thus, the pH-dependent dissolution of the solid facilitates kinetic control over BiNP nucleation and growth by modulating the concentration of soluble bismuth (III) monomer available for reduction. Consistent with this, it was observed that both nucleation and growth rates increase when the synthesis pH was lowered, corresponding with higher available Bi(III) concentration for reduction in more acidic solutions. Also consistent with this, at pH≤8, not enough isolated bismuth(0) nanoparticles are formed to result in a stable aqueous colloid because the saturation concentration for nucleation and growth is too rapidly achieved, resulting in the formation and precipitation of aggregated nanocrystallites. The largest difference in the reaction products synthesized at different pH values is not the individual bismuth nanocrystallite size, but the extent of nanocrystallite aggregation, and thus the size and weight of the bismuth particles where a bismuth particle may comprise one or more bismuth nanocrystallites. If bismuth nanocrystals are formed quickly (e.g., at low pH reactions), multiple nanocrystalline domains may be encapsulated within a single particle. However, if particles are formed slowly, there are fewer present in solution at any given time prior to particle capping (a fast step) by the capping agent (e.g., a dextran polymer), thereby reducing the opportunity for inclusion of multiple bismuth nanocrystals in a single particle and, consequently, reducing the bismuth particle size and tendency for gravitational settling.

1. Carbohydrate-Stabilized Bismuth Particles

Surface-stabilizing ligands, or capping agents, were found to both impart an oxidative stability to the bismuth nanocrystals and colloidally stabilize individual nanocrystals, if particles were formed slowly (e.g., over a duration of 1-10 minutes). In some embodiments, polymers, such as carbohydrates, were used as capping agents. A synthetic protocol was developed to produce aqueous bismuth particles that did not return to a starting bismuth oxide product, and were colloidally stable in solution without aggregation or precipitation.

Medical-grade dextran (a glucose polymer) functions as a biocompatible surfactant used medically as a plasma volume enhancer and to solubilize iron as an intravenous treatment for anemia. As used herein, short-chain, medical-grade dextran (e.g., 75 kDa) functions to surface stabilize the BiNPs while promoting colloidal stability in water and providing protection against hydrolysis. Because release of hydroxide by molecular bismuth hydroxide (1) is the rate limiting step prior to reaction with sodium borohydride (2), adjusting pH controls the formation of BiNPs (3) (Scheme 1). A slower reaction forms dispersed particles, which are individually coated by dextran molecules, whereas fused aggregates form when the reaction proceeds more quickly. In some embodiments, as pH increases, the reaction slows significantly. In one example, when pH increased from 9.0 to 9.8, the time to reach maximum absorbance increased from 3 minutes to 10 minutes.

Experimentally it was observed that a lower reaction pH (i.e., <8.0), produced large aggregates of particles which immediately began to precipitate. Attempting to synthesize colloidally stable nanocrystals, it was found that increasing the reaction pH both slowed the reaction and produced more, smaller, and individual particles than a low pH reaction. Thus, in some embodiments, the system was buffered with the amino acid glycine to control pH. In some embodiments, the particles are synthesized at a temperature from 4° C. to 100° C., such as 25° C. to 75° C. or 30° C. to 50° C. In a working embodiment, particles were synthesized at 40° C. A pH range of 9 to 11 facilitated the growth and capping of colloidally stable particles at 40° C.; below pH 9, reductions occurred too quickly for surface capping of individual particles and aggregates were formed. At a higher pH, no reduction was observed. The pH may be adjusted slightly higher (e.g., up to pH 12) as temperatures increase or slightly lower as temperatures decrease (e.g., down to pH 8).

To terminate the reaction and return the colloidal solution to a neutral pH, phosphoric acid was added dropwise to a very slightly alkaline pH, e.g., to a final pH of 7.4. The phosphate then present in the solution functions as a buffer to stabilize the solution at a physiologically relevant pH.

Figure 3:
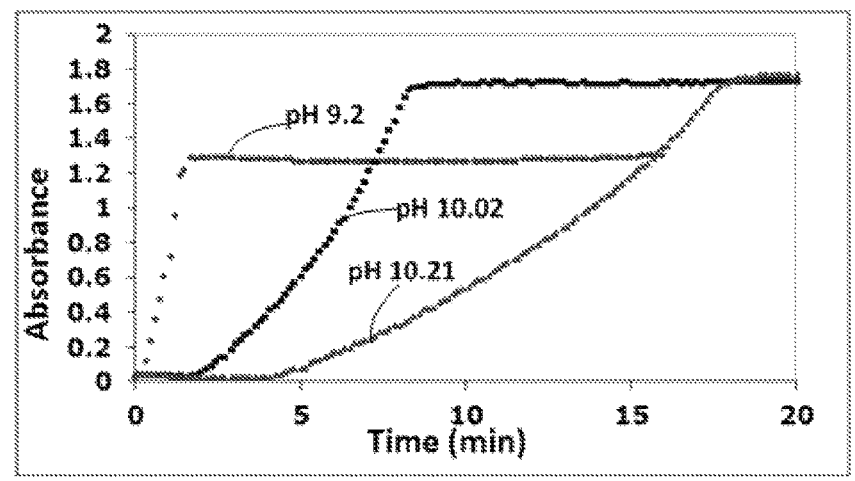
FIG. 3 is a graph of absorbance (at 650 nm) versus time for dextran-stabilized bismuth nanoparticle growth at pH 9.2, 10.02, and 10.21.

To monitor particle formation, the in situ absorbance at a wavelength of 650 nm was measured (FIG. 3). The absorbance curve suggested that the reaction proceeds in three phases: an initial nucleation phase, a particle growth and peak phase, and finally an aggregation and degradation phase. This last phase is a heterogeneous solution showing highly variable absorbance measurements due to the presence of large aggregates. If the reaction is run to its endpoint, a white precipitate forms, indicative of a bismuth oxide species. To compare growth rates under different synthetic conditions, the time to peak absorbance was plotted as a function of pH, and a linear relationship was observed. The linear relationship between time and peak absorbance as a function of pH is consistent with the proposed mechanism. Experimentally it was observed that a lower reaction pH (<8.0), produced large aggregates of particles, which immediately began to precipitate. Thus, a pH range between 9 and 10 appears ideal for the synthesis of large numbers of small stable particles. The size distribution of the bismuth crystallite was found to not be dramatically affected by the synthetic conditions, and slow growth of particles is simply necessary for surfacting individual particles. To terminate the reaction and return the colloidal solution to a neutral pH, phosphoric acid was added dropwise to a final pH of 7.4. The phosphate then present in the solution became a buffer to stabilize the solution at a physiologically relevant pH.

The impacts of several other synthetic factors on particle formation were measured spectroscopically, including the addition of salts, buffers other than glycine and buffer concentration. No discernible effects on the growth of the particles were observed. Increased reducing agent or bismuth concentration did affect the growth rate of the particles, which is not inconsistent with the proposed reaction mechanism.

2. Bismuth Particles with Charged Outer Coatings

In some embodiments, bismuth nanoparticles and/or microparticles with charged outer coatings are synthesized by reducing a bismuth salt in a suitable solvent in the presence of one or more ligands comprising one or more functional groups with the desired charge(s). In working embodiments, the ligands were Tris, which provides an amine group, and tricine, which provides a carboxylic acid group. In certain embodiments, bismuth nitrate (Bi (NO$_3$)$_3$.5H$_2$O) is dissolved in a polyol, e.g., ethylene glycol, along with one or more selected ligands. Desirably, a solvent and solvent volume are selected in which the desired amounts of bismuth salt and the coating agent(s) are soluble. In some instances, temperature may be varied to facilitate dissolution of the bismuth salt and/or coating agent(s). Typically a temperature is selected at which the solvent is in a liquid state, i.e., the temperature is between the freezing and boiling points of the solution. For example, when ethylene glycol is the solvent, the temperature may range from −12° C. to 197 80° C. In some working embodiments, the solution was heated to a temperature greater than 80° C. but below the boiling point of the solution.

A reducing agent is added and the reaction is allowed to progress for a period of time until a persistently black solution is reached. The time to reach this stage may range from a few seconds to several hours, depending upon the temperature, ligand, solvent, and concentrations of each component. In some embodiments, the time may be from 5 seconds to more than 24 hours, such as up to 12 hours, up to 6 hours, up to 1 hour, up to 30 minutes, up to 15 minutes, up to 5 minutes, up to 1 minute, up to 30 seconds, 5 seconds to 5 minutes, 10 seconds to 1 minute, 15-30 seconds, 30 seconds to 5 minutes, 1 minute to 15 minutes, 1 minute to 30 minutes, 15 minutes to 1 hour, 30 minutes to 6 hours, 1-12 hours, or 6-24 hours. Typically, as the temperature increases, the reaction time decreases. For instance, a reaction that is allowed to run for 30 seconds at 80° C. may be run for only 15 seconds at 90° C. The temperature and/or time can be varied to produce particles of a desired size. In a working embodiment, the reducing agent was borane triethyl tetramine, and the reaction was allowed to proceed for 20 seconds at greater than 80° C. The reaction can be quenched by chilling the solution to a temperature, e.g., by adding ice water, at which the reaction cannot proceed. Nanoparticles may be recovered by any suitable method, e.g., centrifugation, filtration, and/or precipitation using a suitable solvent in which the particles are insoluble.

B. Reduction of Bismuth Cations in a Solvent

In some embodiments, bismuth particles coated with solvent molecules are produced. The solvent molecules may be adsorbed to the bismuth particles by electrostatic interactions, such as van der Waals forces or adsorption of electron-dense solvents on electron-poor metal surfaces. Generally, the selected solvent is a polar, amphiphilic solvent, such as an alcohol, amine, carboxylic acid, or organothiol that is a liquid at ambient temperature and/or at a suitable temperature for the reduction. In some embodiments, the temperature ranges from ambient temperature up to the boiling point of the solution. Suitable alcohols include aliphatic alcohols, such as alkyl alcohols, particularly lower alkyl alcohols. Suitable amines include aliphatic amines, e.g., alkyl amines, such as lower alkyl amines. Suitable carboxylic acids include aliphatic carboxylic acids, e.g., alkyl carboxylic acids, particularly lower alkyl carboxylic acids. Suitable organothiols include aliphatic thiols, such as alkyl thiols, particularly lower alkyl thiols. In some instances, an aqueous solution of the alcohol, thiol, or amine may be used.

A bismuth salt is dispersed and/or dissolved in the solvent, and a reducing agent is added. As bismuth cations are reduced, forming elemental bismuth particles, solvent molecules become adsorbed to the particle surfaces. When the solvent is amphiphilic, the polar end of the solvent molecules adsorb to the particle surface, with the non-polar ends protruding from the particles. The solvent coating increases the hydrophobicity of the bismuth particles. Particles may be recovered by any suitable method, e.g., centrifugation, filtration, extraction into a non-polar solvent (e.g., hexanes), and/or precipitation using a suitable solvent in which the particles are insoluble. In working embodiments, bismuth particles with ethanol, octanol, and octyl amine coatings were synthesized by dissolving BiCl$_3$ in the solvent, and reducing the Bi$^{3+}$ cations with sodium borohydride.

In certain embodiments, a single compound may serve as solvent, reducing agent, and/or capping agent. In one example, oleylamine functioned as solvent, reducing agent, and capping agent to produce ~100-nm coated bismuth particles from a Bi(III) salt.

C. Formation of Coated Bismuth Particles from Bulk Bismuth

In some embodiments, coated bismuth particles are formed by milling bulk bismuth in a solvent. This method is also referred to as a "top-down" synthesis since large particles are reduced to smaller particles during the procedure. Bismuth powder is combined with the selected coating/capping agent(s) and subjected to rigorous mechanical mixing, e.g., ball milling, grinding, or a combination thereof. Without being bound by a particular theory, it is thought that mechanical forces break apart the bismuth powder particles, forming bismuth microparticles and nanoparticles, and temporarily producing a clean, reactive surface as metal bonds are momentarily unfulfilled, rendering the surface electrophilic. Coating agent molecules then bond or adsorb to the reactive nanoparticle surfaces. Suitable coating agents for this procedure include hydrophobic or amphiphilic coating agents such as alkanes, alkenes, alkynes, aliphatic carboxylic acids, aliphatic amines, aliphatic alcohols, organothiols (e.g., aliphatic thiols), and/or polymers. In one embodiment, the coating agent is a liquid. In yet another embodiment, the coating agent is a solid at ambient temperature, and the procedure is performed at temperature sufficient to melt the coating agent. In some embodiments, hydrophobic, coated bismuth particles subsequently are extracted into a non-polar solvent (e.g., hexanes) and then dried.

In one example, bismuth powder was ball-milled with oleic acid and extracted into hexanes, then dried to yield oleic acid-coated bismuth nanoparticles. In other examples, bismuth was milled with 1-decane, 1-decene, 1-pentene, or styrene. Pentene-capped particles were washed in hexanes and dried before use. Styrene-capped particles were washed in toluene and dried before use. In another example, bismuth was milled with dihydroxyacetone, and the resulting particles were washed with water and dried before use.

D. Surface Ligand Exchange

In some embodiments, a coated bismuth particle is formed with a first capping agent, or ligand, and the first capping agent is subsequently exchanged in a second step for another capping agent that has a greater affinity for the bismuth surface. For example, an elemental bismuth surface has an affinity for surface ligand donor atoms following the preference N<O<S. Thus, a bismuth particle coated with adsorbed primary amine ligands may be synthesized using an aliphatic amine capping agent, e.g., oleylamine. The amine ligands subsequently can be exchanged for alcohol (ROH), carboxylate (RCOO—), or thiol (RSH) ligands.

IV. Applications

Bismuth has several advantages that make it an attractive candidate for radiopaque applications. Bismuth is abundant and therefore inexpensive. It is also biologically well tolerated. Bismuth is the heaviest, naturally occurring stable element with only minimal radioactivity. $^{209}$Bi decays very slowly via alpha decay into thallium-205, and has a half-life of $1.9 \times 10^{19}$ years. Bismuth has a high X-ray opacity, with a higher atomic number (83) than either gold (79) or lead (82). Bismuth is also very dense, with a density at room temperature of 9.78 g/cm$^3$. In some embodiments, the bismuth particles have a bismuth core with a diameter of less than 20 nm, less than 50 nm, less than 100 nm, less than 500 nm, less than 1 µm, less than 10 µm, less than 25 µm, less than 50 µm, less than 100 µm, less than 150 µm, or less than 250 µm, providing small, dense particles that are radiopaque. Additionally, the surface of the bismuth particles is chemically customized to provide desirable material properties, e.g., miscibility, solubility, etc.

Embodiments of the disclosed bismuth microparticles and nanoparticles are suitable for many applications, including but not limited to X-ray opaque surgical sponges, cell-targeted in vivo medical imaging, X-ray contrast agents (e.g., for intravenous and/or intra-articular injection), X-ray protective clothing, X-ray photolithography masks, X-ray opaque ink, non-destructive testing of metal cast parts, such as crack and defect testing, evaluation or research of structures, and security/location tags or labels, such as anti-counterfeiting security labels. Exemplary applications are described in Table 1, with additional details provided for certain applications below.

TABLE 1

| Category | Matrix Material | Exemplary Coating/Capping Agents | Exemplary Particle Sizes | Example Applications |
|---|---|---|---|---|
| Medical polymers | polyurethane | dihydroxyacetone<br>glucose<br>ethanolamine | 20-100 nm | catheter/stent |
| | silicone | alkenes (e.g., 1-decene, 1-pentene) | | surgical sponge/<br>surgical item tag |
| | latex | dihydroxyacetone<br>alkenes (e.g., 1-pentene)<br>polyacrylic acid | | |
| | poly(tetrafluoro-ethylene) | 1-pentene<br>1-decene<br>perfluorinated alkyl phosphonates<br>perfluorinated alkyl siloxanes | | vascular grafts, nonstick coatings for medical implants |
| Ink | polystyrene binder | styrene | 5-50 nm | security or inventory tags |
| | water-based, dextran binder | carbohydrates/sugars<br>dihydroxyacetone<br>polyacrylic acid<br>polyvinylpyrrolidone<br>thiocarboxylates | | |
| | linseed oil | 1-decene<br>1-pentene<br>oleylamine<br>alkanethiols | | |
| | wax-based inks | alkanethiols | | |
| Industrial plastics | polypropylene | 1-decene<br>1-pentene<br>lower alkanethiols | 500 nm-1 µm | location tags for plastic items such as toys, parts or structures of a device |
| | polystyrene<br>polyethylene-terephthalate | styrene<br>alkylammonium ligands<br>alkylquinolinium ligands | | |
| | poly(methyl methacrylate) | dihydroxyacetone<br>polyvinylpyrrolidone<br>thiocarboxylate<br>carboxylic acids | | |
| Flowable contrast agents | water<br>toluene<br>non-polar organic solvents | glucose<br>styrene<br>1-decene | 5-50 nm | crack and defect testing for cast parts, or negative contrast agent for evaluation or research of structures |
| Glasses | silica-based glass | carbohydrates/sugars<br>alcohols<br>alkanolamines | | X-ray opaque glass |

A. Radiopaque Surgical Sponge

Unfortunately, surgical sponges may inadvertently be left inside of patients after surgery. When this occurs, serious medical issues can arise. Consequences of infection or a perforated bowel, which can lead to death, are possible. Further issues such as lawsuits and secondary surgeries also arise. Some statistics suggest that the chance of a sponge being left inside a patient after surgery is approximately one out of every eight thousand surgeries. A study by the Harvard School of Public Health estimates that the financial cost of a retained surgical sponge is about $200,000 per incident (Regenbogen et al., *Surgery* (2009) 145(5):527-535).

Currently available X-ray opaque sponges simply do not work well because they are not sufficiently X-ray opaque to detect reliably with X-rays and/or CT scans. In one study, approximately 10% of X-ray opaque retained surgical sponges were not visible on X-rays (Geiger et al., "Intraoperative Imaging for Foreign Body Detection," UCSF Medical Center, Apr. 13, 2009, available at http://www.radiology.ucsf.edu/patient-care/patient-safety/retained-surgical-objects). Additional strategies for reducing the incidence of retained sponges include manual sponge counts before and after surgery, bar code systems (where each sponge has a bar code that is scanned at the time of placement and again at the end of surgery), and radio frequency identification (RFID) sponges (where sponges have an RFID tag that can be detected with an RFID sensor after surgery).

Figure 12:
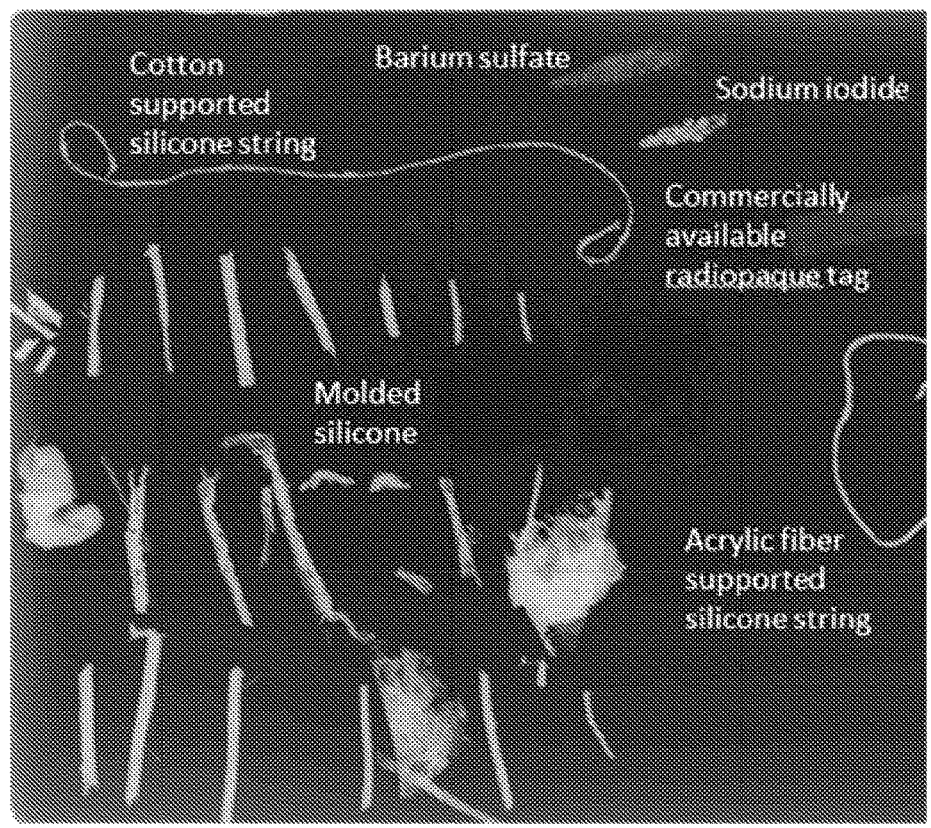
FIG. 12 is an X-ray image showing a cotton string, an acrylic string, and several pieces of molded silicone impregnated with embodiments of the disclosed bismuth particles. For comparison of X-ray opacity, NaI and $BaSO_4$ powders and a commercial radiopaque sponge are also shown.
Figure 13:
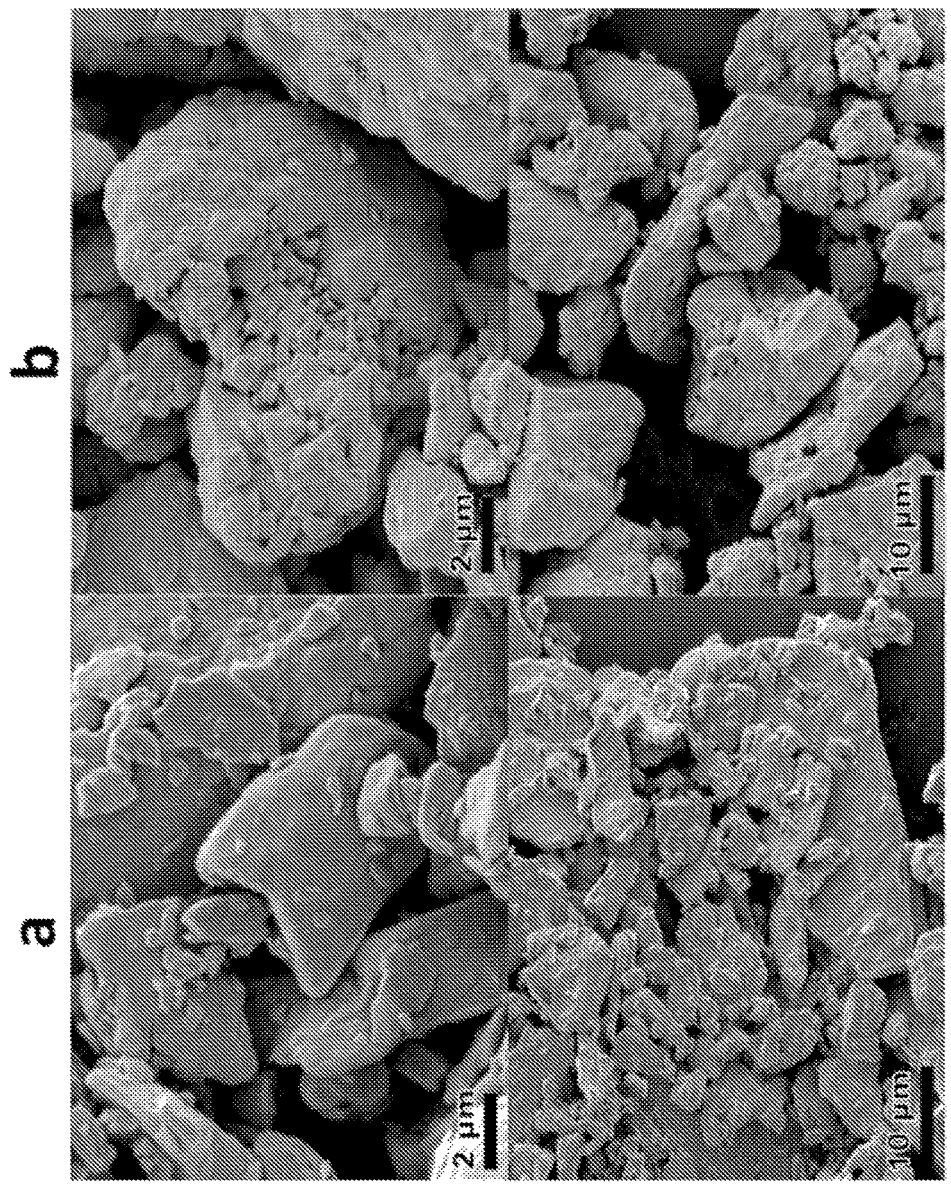
FIGS. 13a-b are SEM micrographs of bismuth particles coated with 1-pentene and 1-pentane, respectively. The top images are shown with a 2-μm scale bar; the bottom images are shown with a 10-μm scale bar.

In some embodiments, a member, such as a string or a disk, impregnated with bismuth particles is attached to, or incorporated into, a surgical sponge by any suitable means, such as by sewing or otherwise adhering the member to the sponge. An X-ray or CT scan of a patient's surgical site after surgery will visualize the bismuth-impregnated member, thereby enabling medical personnel to locate and remove the sponge. Advantages of the bismuth-tagged sponge include its low cost, biocompatibility, and minimal effect on existing operating room procedures and protocols. In a working embodiment, bismuth microparticles and/or nanoparticles were coated with hexanes and dispersed into unpolymerized silicone. Cotton or acrylic strings were soaked in the bismuth/silicone mixture and allowed to dry. The prepared strings were substantially radiopaque (FIG. 12, right side of image; FIG. 13, left side of image). As shown in FIG. 12, commercially radiopaque surgical sponges (left side of image) are substantially less visible than the bismuth-impregnated string in the X-ray image. FIG. 13 demonstrates that the bismuth-impregnated strings are X-ray visible even when embedded within an object and/or covered by additional objects.

B. Radiopaque Plastics

Young children and some animals are prone to swallowing small objects, such as small plastic toys or toy parts. Surgical equipment and/or prosthetics may be plastic or may include plastic parts. Surgical equipment may be intentionally or unintentionally left in a patient's body. Under such circumstances, it may be desirable or necessary to locate the internalized plastic object. However, internalized plastic items are difficult to visualize with X-rays.

Embodiments of the disclosed bismuth microparticles and nanoparticles, particularly hydrophobically-coated bismuth particles, are suitable for inclusion into plastic toys, plastic surgical equipment, plastic prosthetics, and other plastic objects. The hydrophobic nature and small size of the particles facilitate incorporation into plastic without substantial alteration and/or compromise of the polymeric matrix structure. Plastic objects including embodiments of the disclosed particles can be visualized with X-rays.

In some embodiments, the particles may be incorporated throughout the plastic object. However, it may be desirable from a manufacturing and/or cost standpoint to only include bismuth particles in a portion of the object. In such embodiments, a radiopaque tag comprising a small piece of plastic with incorporated radiopaque bismuth particles may be embedded in the toy, surgical equipment, prosthetic, or other plastic object. Visualizing the radiopaque tag enables the user to detect and localize the plastic object.

C. Radiopaque Ink

Embodiments of the disclosed bismuth particles can be incorporated into inks, such as water-based inks or wax-based inks. The resulting radiopaque inks can be used, e.g., to make medical or inventory tags. In one embodiment, a bismuth-particle ink can be used to print a radiopaque barcode label, to print a security tag, or to mark an object for security or shipping/transportation applications. In another embodiment, a bismuth-particle ink can be used to print a lithographic mask onto a substrate when the substrate will be etched using an X-ray light source.

D. Radiopaque Labels/Tags

Embodiments of the disclosed bismuth particles can be incorporated into labels or tags, such as self-adhesive labels/tags. For example, bismuth particles can be incorporated to a polymer-based label. Depending on the desired utility, the adhesive may form a permanent bond or a temporary, removable bond to an object, such as a plastic object. Such labels may find utility in many applications, including as security tags or surgical equipment labels. Advantageously, the labels can be applied by the end-user to non-radiopaque plastic surgical equipment.

E. Radiopaque Contrast Agents

In one embodiment, the disclosed bismuth particles may be dispersed in biocompatible solutions to provide X-ray contrast agents suitable for intravenous and/or intra-articular administration. For example, bismuth particles with a hydrophilic coating, e.g., a carbohydrate coating, may be dispersed in a pharmaceutically acceptable aqueous solution. In another embodiment, the disclosed bismuth particles may be dispersed in a solution for leak and/or crack detection in a non-radiopaque object.

V. Examples

Example 1

Synthesis and Characterization of Bismuth Glyconanoparticles with a Dextran/Water Coating Reagents:

Bismuth nitrate pentahydrate (Acros organics 98%), glycine (Acros, 99+% Analysis grade), potassium hydroxide (reagent grade), dextran (Carbomer Inc., 75,000 MW, clinical grade), sodium borohydride (MP Biomedicals, 98-99%), and phosphoric acid (>85%, Sigma-Aldrich) were purchased and used as received without further purification. All stock solutions were prepared using fresh electrophoretically pure $H_2O$ (18 MΩ resistivity).

Synthesis:

In a typical synthesis, 250 mg (0.52 mmol) $Bi(NO_3)_3 \cdot 5H_2O$ was suspended by sonication in 25 mL $H_2O$. During the reaction temperature was held constant at 40° C. by immersion of the reaction vessel in a temperature controlled water bath. All reactions were performed with magnetic stirring at >800 rpm. 10 mL of a 2M glycine solution (20 mmol) was added with an appropriate amount of 2M KOH to achieve a desired pH (e.g., approximately 12 mL for pH 9.0). Then, 7.5 mL of a 100 mg/mL medical-grade dextran stock solution was added immediately prior to the addition of 12.5 mL freshly prepared 10 mg/mL (3.3 mmol) $NaBH_4$. After approximately 5 minutes, when the reactions appeared to have stabilized by visualization (based on color change) and cessation of gas evolution ($H_2$ from $BH_4^-$), the solutions were brought to pH 7.4 by dropwise addition of 1.0 M $H_3PO_4$. Samples were briefly sonicated to promote dispersion, and were allowed to stir for an hour at room temperature before purification.

Upon addition of reducing agent, the solutions were observed to change from a cloudy, colorless solution or white suspension to a brown solution, and ultimately an opaque black solution in a timeframe dependent on the initial pH of the reaction (FIGS. 2a-2e). The elapsed time to obtain an initial brown color, indicative of the beginning of particle nucleation, and the elapsed time to obtain a stable black color, indicative of the formation of larger bismuth(0) nanocrystallites, were noticeably longer with increased reaction pH. In the absence of dextran, black BiNPs were visibly formed (the rhombohedral bismuth(0) phase was confirmed by powder X-ray diffraction) upon addition of the reducing agent to the aqueous bismuth(III) precursor; however, these bismuth(0) particles quickly aggregated, precipitated out of solution (FIG. 2f), and eventually underwent oxidation and hydrolysis, resulting in the formation of an unidentified white amorphous solid.

Dialysis and Purification:

The reaction mixture was dialyzed against nanopure water using Spectra/Por® dialysis tubing (nominal MWCO 50,000, Spectrum® Laboratories, Inc.) to remove salts, excess starting reagents, and small molecule byproducts, producing nanoparticle solutions of greater than 99% purity. The suspension was centrifuged at 3.0 RCF (relative centrifugal force) for 10 minutes to remove large aggregates. Nanoparticles in the supernatant were concentrated by rotary evaporation under vacuum (40° C. water bath) and stored at room temperature away from light. For long-term storage, samples were stored in water either at −20° C. or at 4° C. with a trace amount of sodium azide to prevent biological contamination.

UV-visible spectra were collected on a Shimadzu UV-2450 UV-visible spectrophotometer in standard 1-cm disposable polystyrene cuvettes.

UV-Visible Spectroscopy and Kinetics:

10 mL of stock reaction solutions were prepared containing 5.15 μmol dissolved $Bi(NO_3)_3.5H_2O$, 100 μmol glycine, and 75 mg dextran. KOH was added to achieve desired pH values in the range of 8-10. The reactions were prepared as follows: 1) appropriate volumes of the Bi(III), glycine and KOH solutions were added to and mixed in 8.0 mL $H_2O$; 2) the pH was measured; 3) dextran solution was added; and 4) $H_2O$ was added as needed to bring the final volume of each solution to 9.9 mL. Each sample then was divided into three equal-volume aliquots, which were monitored simultaneously by UV-visible spectroscopy on a Varian Cary® 100 Bio spectrophotometer equipped with stirring capabilities. Light attenuation (due to absorption and scattering by the BiNPs) was measured at 650 nm every 5 seconds after the addition of sodium borohydride solution (37.5 μL, 10.57 μmol) to each cuvette at t=0 s. Data was collected simultaneously from replicates at each pH and recorded in parallel. Attenuation values at teach time point from the three replicates for each pH were averaged and plotted versus elapsed time. For consistency, all samples were prepared, mixed, and measurements initiated within 90 seconds. These small-scale spectroscopic experiments allowed real-time observation of reaction stages and trends in reaction rates as a function of pH. Qualitatively, the same trends in nucleation periods and growth rates were observed in the large-scale preparations, although the colloids produced in the large-scale preparations were, in general, colloidally stable for longer time periods (days versus hours).

A plot of attenuation versus time (FIG. 3) indicates that the reactions proceeded in three phases: an initial nucleation phase with no attenuation, a particle growth phase indicated by a dramatic increase in attenuation as the black particles formed, and finally a steady-state phase indicated by a plateau in attenuation. Under certain conditions, (e.g., low (<8) pH syntheses), a fourth aggregation phase was observed (FIG. 10, which was evidenced by loss of attenuation as the particles precipitated.

The time period of the nucleation phase was pH dependent, and was longer at higher pH values. The rate of particle growth, as indicated by the change in attenuation with time (i.e., the slope of the growth regime in FIG. 2), was also pH dependent, and was slower at higher pH values, producing a greater number of individual Bi(0) nanocrystals. Regardless of synthesis pH, all samples reached an absorbance plateau corresponding to a steady-state phase in which the solution composition did not appear to change with time.

Experimentally, it was observed that at a low reaction pH (≤8.0), large aggregates of elemental Bi particles formed in the presence of dextran; these particles did not oxidize or decompose, as evidenced by the black color of the precipitated solid and confirmation of the rhombohedral bismuth(0) phase by powder X-ray diffraction. However, the large aggregates of elemental BiNPs synthesized at pH≤8.0 could not be redispersed in water, even with sonication, to achieve stable aqueous colloids. Increasing the reaction pH (up to pH=10.5) produced a greater number of isolated BiNPs that did not undergo gravitational settling, thus resulting in stable, aqueous Bi glyconanoparticle colloids. At pH values above 11, no reaction was visually or spectroscopically observed, presumably due to lack of soluble bismuth(III) available for reduction. For colloidally stable samples synthesized in solutions with pH between 9 and 10, dilute phosphoric acid was added dropwise to achieve final solutions at a physiologically relevant pH of 7.4 without loss of either colloidal or chemical stability.

The impact of a variety of other synthetic factors on particle formation kinetics and product colloidal stability was measured spectroscopically, including the addition of salts (e.g., NaCl, $KNO_3$), buffering agents other than glycine (e.g., bicine, tris), and buffer concentration. In all cases, pH-dependent nucleation and growth periods were observed with the colloidal stability correlated to synthesis pH more than any other factor. The most stable colloids were achieved in solutions between pH values of 9 and 10.

Transmission Electron Microscopy:

Transmission Electron Microscopy (TEM) was performed on FEI Tecnai F-20 TEM operating at 200 kV. Purified samples were drop-cast on holey carbon copper-supported grids (Ted Pella, Inc.), and dried for 2 hours at 150° C. prior to imaging. Energy dispersive X-ray spectroscopy (EDX) was performed on a representative sample on 20 individual particles during TEM imaging.

Figure 4:
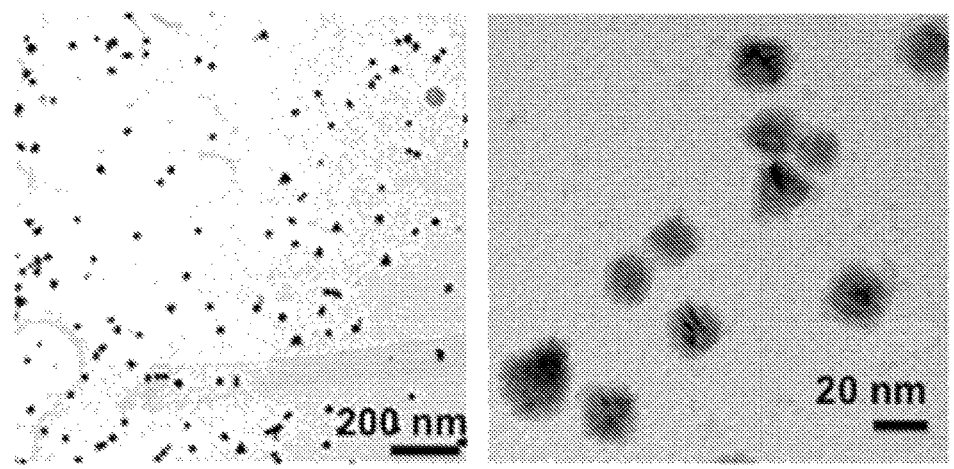
FIG. 4 is a pair of transmission electron microscopy (TEM) micrographs showing dextran-stabilized bismuth nanoparticles prepared according to one embodiment of the disclosed method.
Figure 5:
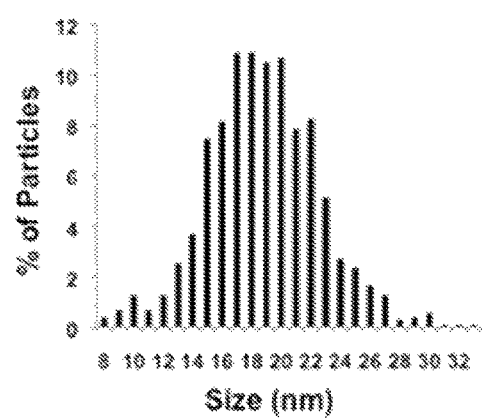
FIG. 5 is a graph illustrating the bismuth core size distribution of dextran-stabilized bismuth nanoparticles prepared according to one embodiment of the disclosed method.
Figure 6:
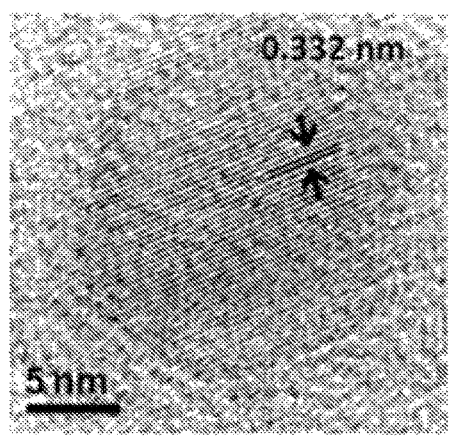
FIG. 6 is a high-resolution TEM image illustrating the lattice fringes and diffraction line spacing of dextran-stabilized bismuth nanoparticles prepared according to one embodiment of the disclosed method.

FIG. 4 includes two TEM images of bismuth nanoparticles formed as described above. Various crystallite morphologies were observed, regardless of synthesis pH, including: spheres, triangles, hexagons, and rods. However, >50% of particles were spherical in all cases. FIG. 5 is a graph illustrating the bismuth core size distribution; 1040 particles synthesized at a pH of 9.97 were counted from the TEM images and found to have a mean particle diameter of 19.5±3.7 nm. Under high-resolution TEM, a lattice fringe spacing of 0.332 nm was measured, consistent with the d-spacing (0.328 nm) corresponding to the [012] planes of bulk elemental bismuth (JCPDS Card No. 00-044-1246) (FIG. 6). Pairing TEM imaging with topographic EDX analysis of 20 particles using the same sample grid, and only elements Bi, O, C and Cu (from the grid) were found. The presence of bismuth was localized to the particles, i.e., no bismuth was found outside of the dark crystallites on the TEM grid.

Figure 7:
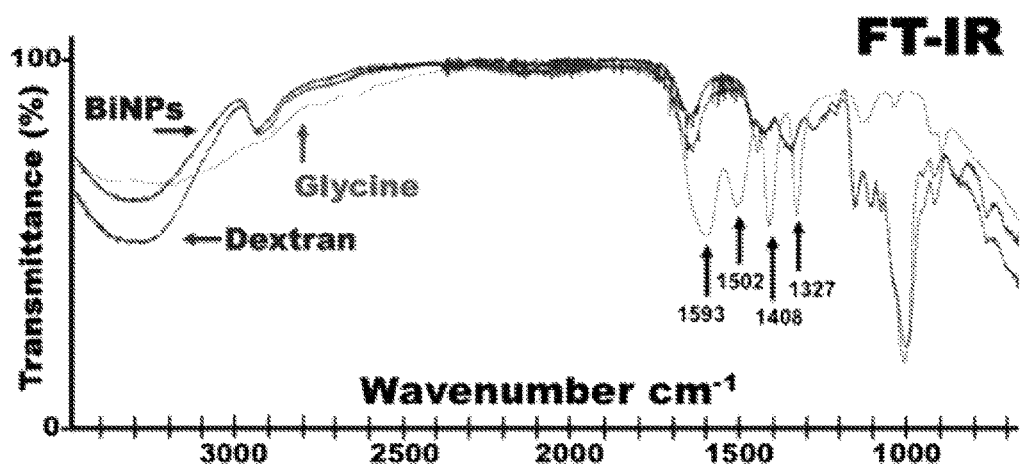
FIG. 7 depicts the IR spectra of dextran-stabilized bismuth nanoparticles prepared according to one embodiment of the disclosed method. For comparison, IR spectra of dextran and glycine are also shown.

FT-IR Spectroscopy:

FT-IR spectroscopy was performed on a Thermo Scientific Nicolet iS10 spectrophotometer equipped with a single-bounce diamond ATR attachment. Aqueous solutions of purified BiNPs, dextran, and glycine were drop-cast onto the ATR crystal, and the solvent was evaporated as necessary using a heat gun to deposit a sample film for analysis. IR spectra of bismuth nanoparticles, dextran, and glycine are shown in FIG. 7. During synthesis, the bismuth nanoparticles are surface stabilized by dextran. Accordingly, the FTIR spectrum of the dextran-stabilized bismuth nanoparticles is substantially identical to the FTIR spectrum of dextran. The bismuth nanoparticle spectrum includes no FTIR peaks characteristic of glycine. Importantly, the absence of a carboxylate peaks at 1593, and 1408, and amine deformation between 1527 and 1502 (Suzki 1963) suggest that glycine served only as a buffer during synthesis but did not become part of the BiNP complex and was removed during purification. Because the particles appear to be coated solely in dextran, they are bismuth glyconanoparticles.

XPS (X-ray photoemission spectroscopy) of the nanomaterial is consistent with spectra collected for a variety of $Bi_2O_3$ thin films (Dharmadhikari et al., *J. Electron Spectroscopy and Related Phenomena*, 1982, 25, 181). Because no evidence of bismuth oxide was observed by other techniques, it is thought that the nanocrystals are terminated in a thin layer of amorphous bismuth oxide.

Figure 8:
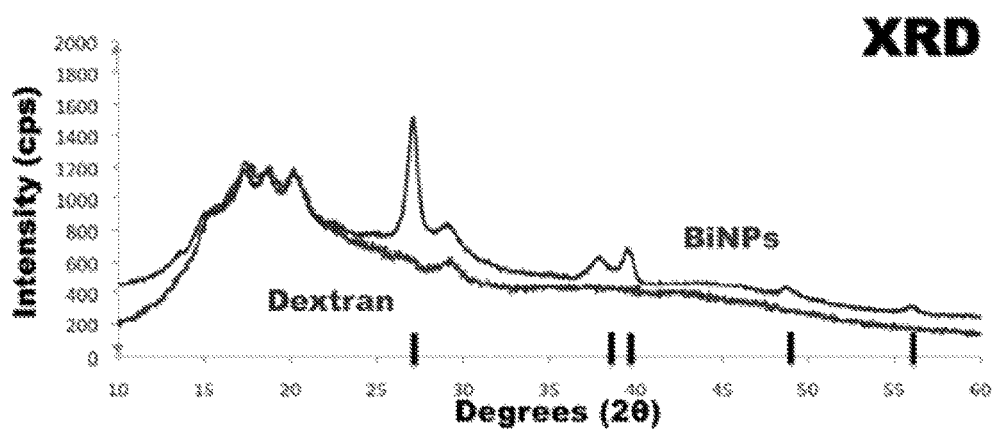
FIG. 8 depicts X-ray powder diffraction patterns of dextran-stabilized bismuth nanoparticles prepared according to one embodiment of the disclosed method and dextran. The X-ray diffraction pattern for dextran is shown for comparison.

X-Ray Powder Diffraction Analysis:

Concentrated BiNP samples were evaporated to dryness in a ceramic evaporation dish in air, milled into a fine powder, and pressed onto a glass slide. Data were collected in focused beam (Bragg-Brentano) geometry mode on a Rigaku Ultima IV X-ray diffraction instrument using Cu $K_\alpha$ radiation. Scans were performed over the angular range from 5-85° 2θ at a scan rate of 0.25°/min at room temperature. The X-ray powder diffraction spectra are shown in FIG. 8. The resulting diffraction pattern contained peaks for rhombohedral elemental bismuth (PDF card 00-044-1246, tick marks indicated calculated reflections), consistent with the high-resolution TEM analysis. Other peaks apparent in the spectrum (17.52, 18.83, 20.25, and 28.8° 2θ) were identified as crystallized dextran. The bismuth nanoparticle spectrum demonstrated that the nanoparticles comprise elemental bismuth and crystallized dextran.

Dynamic Light Scattering:

Dynamic Light Scattering (DLS) measurements were taken on a Horiba LB-500 dynamic light scattering instrument. Samples were purified as described above, diluted in $H_2O$, and passed through a 0.45 μm PTFE syringe filter prior to measurement. Measurements (300 scans) at five concentrations of each sample were performed to determine a size distribution independent of concentration or inter-particle interaction effects (e.g., multiple scattering).

Glycoparticles (i.e., dextran-stabilized particles) synthesized at pH 9.97 had an average hydrodynamic radius of 65 nm, with a minimal cutoff of 30 nm, after filtering through a 0.45 μm syringe filter. After filtering through 0.2 μm and 0.1 μm syringe filters, the mean sizes dropped to 38 nm and 24 nm, respectively. The minimal size cutoff also shifted, indicating that syringe filtering altered the glycoparticles by reducing the surfactant hydrodynamic radius.

The difference, 110 nm, between the crystallite size (19.5 nm) and hydrodynamic diameter (130 nm) can be attributed to a dextran and water coating, which presumably imparts the colloidal stability on the glycoparticles. A sharp lower limit cutoff of the 50,000 MW dialyzed particles at 30 nm is most likely a result of a size selection by dialysis. Syringe filtering through smaller pore size filters altered the hydrodynamic coating, but not crystallite size. The 0.1 μm filter did not appear to remove the colloid population above 100 nm, but surprisingly the entire particle population shifted down suggesting dextran removal during the filtering process.

pH, Light and Temperature Stability:

To examine the colloidal stability of particles over time, pH range, light conditions, temperature, visual observations, and UV-vis spectroscopy were used to monitor colloidal solutions. Purified particles (dialyzed, centrifuged and concentrated) were diluted in 1 M phosphate buffers and adjusted with KOH to a pH range from 2-12 for pH stability experiments; these samples were protected from light. Additionally, two samples were redispersed in water; one was stored in the dark, and the other was exposed to sunlight. Visual observation and UV-visible spectroscopy were used to monitor the colloidal stability, which was indicated by maintenance of a dark solution color and the absence of precipitates.

Figure 9:
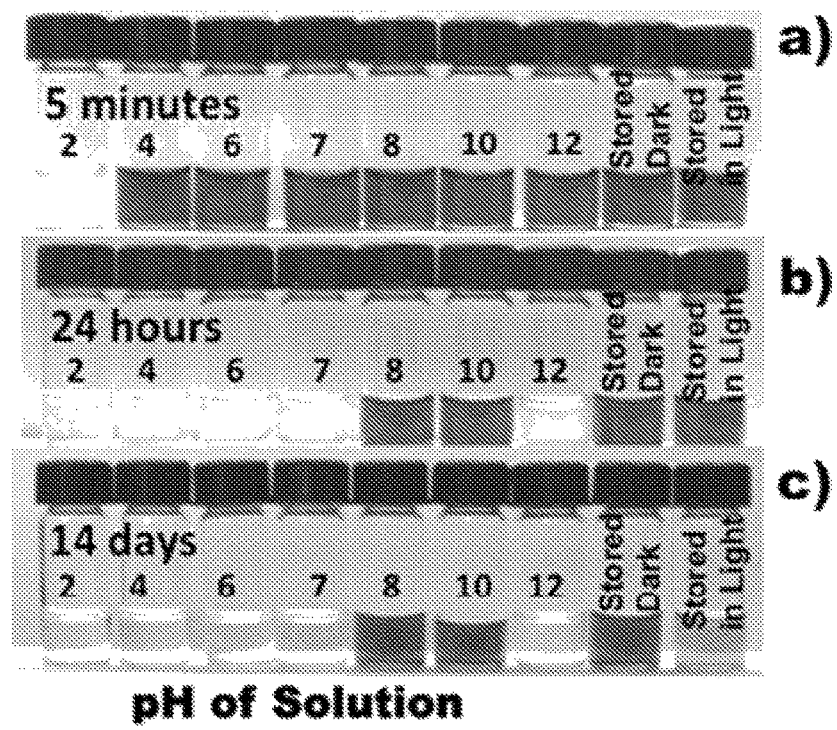
FIGS. 9a-c are photographs illustrating the pH stability over time of dextran-stabilized bismuth nanoparticles prepared according to one embodiment of the disclosed method. Photographs were taken after 5 minutes (FIG. 9a), 24 hours (FIG. 9b), and 14 days (FIG. 9c).

As seen in FIG. 9, when BiNPs were introduced to the solution at pH 2, the particles immediately dissolved, as evidenced by the loss of solution color and the absence of precipitate. Samples at pH values of 4, 6, 7 and 12 initially retained their color, but fully dissolved to yield colorless solutions within 24 hours; the low pH results suggest that the acidic environment of a lysosome would decompose these particles in vivo. However, samples redispersed in solutions at pH 8 and 10 were colloidally stable for over one month, as was a control sample diluted in nanopure water. The latter result suggests that phosphate ions may assist degradation over some pH range.

For light stability experiments, colloids were diluted 1:1 in $nH_2O$ in glass scintillation vials. One sample was exposed to ambient light, and one sample was protected from light by a single layer of aluminum foil. both samples were placed side by side in a window. After two weeks, the sample exposed to light had decreased in color (FIG. 9c).

Figure 10:
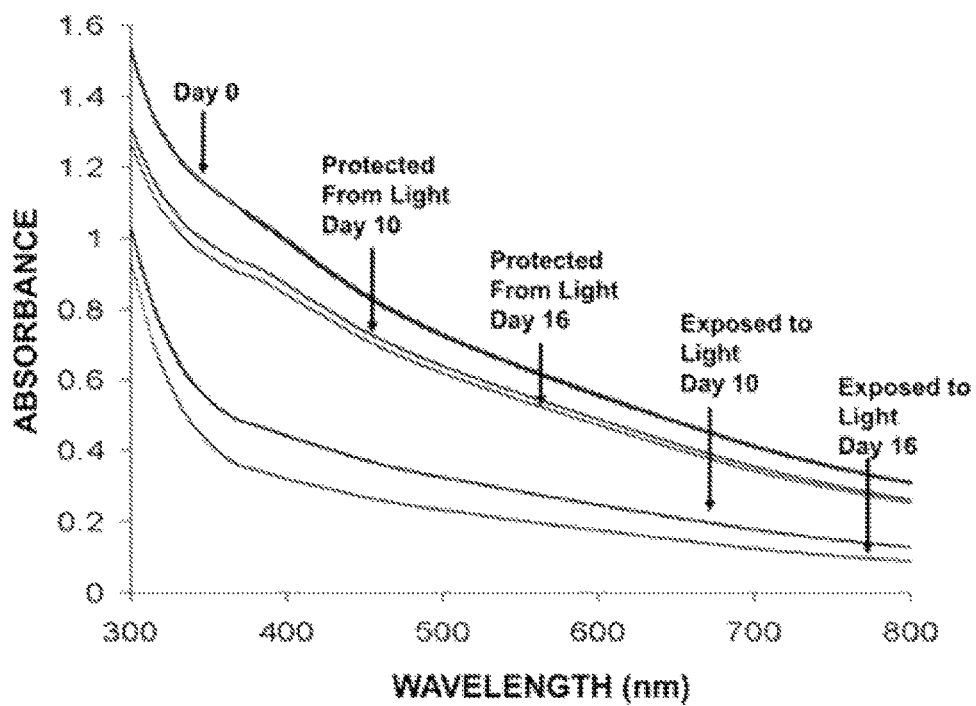
FIG. 10 is a series of UV-visible spectra of dextran-stabilized bismuth nanoparticles prepared according to one embodiment of the disclosed method after being exposed to light for varying periods of time.

To spectroscopically monitor photodegradation, a dilute solution of particles was initially divided into two cuvettes and the absorbance profile was measured daily over a period of 16 days (FIG. 10). One cuvette was wrapped in aluminum foil and both cuvettes were placed side by side in a window; care was taken not to agitate the samples between measurements in case particle settling or precipitate formation occurred. On day zero, both samples showed identical broad absorption spectra, covering the entire visible range with a slight shoulder apparent around 375 nm. The sample constantly exposed to light subsequently lost absorbance intensity uniformly across the visible spectrum as particles decomposed, changing from a dark solution to a light brown color slowly over the course of several days. Conversely, the light-protected sample appeared to be much more stable, as evidenced by a much slower low of color over time. The photo instability of the colloids was unsurprising given their high visible light absorption cross-section, and may indicate an alternative clearance route for elemental BiNPs employed as XCAs.

Particles were also tested for temperature sensitivity by freezing and boiling BiNP samples redispersed in nanopure water. BiNP samples diluted in water and heated to boiling for greater than an hour remained colloidally stable without loss of solution color or precipitate formation. Additionally, water-dispersed BiNPs were slowly frozen at −20° C. or rapidly frozen in liquid nitrogen. Neither treatment reduced color or colloidal stability of the particle solutions upon thawing, indicating that the bismuth glyconanoparticle colloids are robust over a wide range of temperatures.

Example 2

Radiopaque Strings

Reagents:

Bismuth powder, 99.5%, 100 mesh (approximately 150 μm particles) was obtained from Acros Organics (#318091000), and oleic acid were purchased and used without modification. General Electric Premium waterproof clear silicone (100% silicone, #51220) was purchased from a building supply store and used without modification.

Synthesis:

Desired amounts of silicone and bismuth powder were measured (see Table 2). Bismuth powder was coated with hexanes and then mixed with the unpolymerized silicone with mechanical stirring and sonication. The volume of hexanes was sufficient to just wet the bismuth powder without having excess liquid hexanes present. A cotton string then was stirred into the mixture, removed and dried at ambient temperature. The silicone polymerized during the drying process, forming a silicone-bismuth particle coating on the string. The stirring and drying steps were repeated until the majority of the bismuth solution was adhered to the string.

TABLE 2

| Trial | Silicone Mass (g) | Bismuth Mass (g) |
|---|---|---|
| 1 | 1.0975 | 0.5925 |
| 2 | 1.0303 | 1.2232 |
| 3 | 1.0798 | 2.4011 |
| 4 | 1.0886 | 4.0038 |
| 5 | 0.5227 | 0.3204 |
| 6 | 1.0222 | 6.2484 |
| 7 | 0.4548 | 7.4849 |
| 8 | 0.2591 | 5.100 |

To increase particle dispersion in the silicone, bismuth powder was coated with oleic acid. Bismuth powder and excess oleic acid were combined and ball milled for one hour. The oleic acid-coated bismuth particles were extracted into hexanes to separate the coated bismuth particles from the excess oleic acid. Dried powder, 1.5420 g was then combined with 0.1383 g silicone and layered onto a cotton string.

In another trial, bismuth powder was wetted with hexane and mixed with silicone in a ratio of 10.2012 g bismuth particles to 1.0578 g silicone. An acrylic fiber string was stirred into the mixture, removed and dried at ambient temperature. The silicone polymerized during the drying process, forming a silicone-bismuth particle coating on the string. The stirring and drying steps were repeated until the majority of the bismuth solution was adhered to the string. The coated acrylic string showed excellent radiopacity (FIG. 12).

Figure 11:
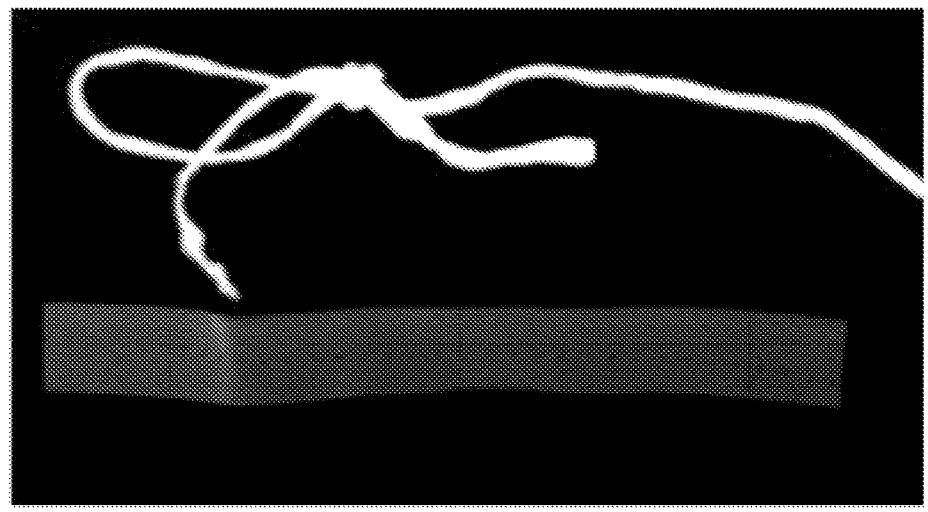
FIG. 11 is an X-ray image of a commercially available radiopaque surgical sponge and a string impregnated with one embodiment of the disclosed bismuth particles.

Results:

All strings showed substantial X-ray opacity (FIGS. 11 and 12). However, as ratios increased, structural integrity decreased as the dried polymeric matrix became brittle and flaked off the string. Trial 7 produced the best results for bismuth/silicone on a cotton string with respect to opacity and structural integrity. FIG. 11 is an X-ray image of one embodiment of a bismuth/silicone-coated string 100 and a commercially available radiopaque sponge 110. FIG. 12 is an X-ray image showing one embodiment of a bismuth/silicone-coated cotton string, a bismuth/silicone coated acrylic fiber string, and several pieces of molded silicone comprising bismuth nanoparticles. For reference, samples of barium sulfate and sodium iodide also are included, along with a commercially available radiopaque tag.

Example 3

Comparison of Alkanes and Alkenes as Capping Agents

Bismuth particles coated with pentane or 1-pentene were prepared by milling 5 g of elemental bismuth in a stainless steel mill with tungsten carbide balls for 20 minutes in the presence of 10 mL solvent. The resultant powder was passed through a 45-μm mesh sieve with addition of hexanes.

FIGS. 13a-13b are SEM micrographs of 1-pentene-capped bismuth particles and pentane-capped bismuth particles, respectively. The results demonstrated that alkene capping agents provide superior colloidal stability with less aggregation than analogous alkanes. Without being bound by a particular theory, it is thought that mechanical forces break apart the bismuth powder particles, forming bismuth microparticles and nanoparticles, and temporarily producing a clean, reactive surface as metal bonds are momentarily unfulfilled, rendering the surface electrophilic. Thus, alkenes may be more effective capping agents because the alkene double bond has a greater electron density than a single bond and is more likely to adsorb to the bismuth surface.

Example 4

Compositions Including Coated Bismuth Particles Prepared by Top-Down Synthesis

General Procedure:

Top-down synthesis typically was performed by milling 5 g of elemental bismuth in a stainless steel mill with tungsten carbide balls for 20 minutes in the presence of 10 mL solvent or 5 g of coating agent.

A. Pentene-Capped Bismuth Particles in Silicone:

9.472 g bismuth was milled in 10 mL 1-pentene for 20 minutes. The resultant powder was passed through a 45-μm mesh sieve with addition of hexanes. The dried powder was scraped and used. The powder was mixed with silicone in varying weight ratios. For example, 90 wt % bismuth in silicone was prepared by mixing 2.05459 g liquid silicone and 17.9356 g 1-pentene-capped bismuth particles in the presence of 5 mL hexanes and molded in a Teflon® mold. Additional samples were prepared that included 11.92 wt %, 19.38 wt %, 32.5 wt %, 45.46 wt %, 48.3 wt %, 67.7 wt %, 71.9 wt %, 74.8 wt %, 75.6 wt %, 82.3 wt %, 82.88 wt %, 84.8 wt %, 85.7 wt %, 89.0 wt %, 92.07 wt %, and 92.3 wt % bismuth.

Figure 14:
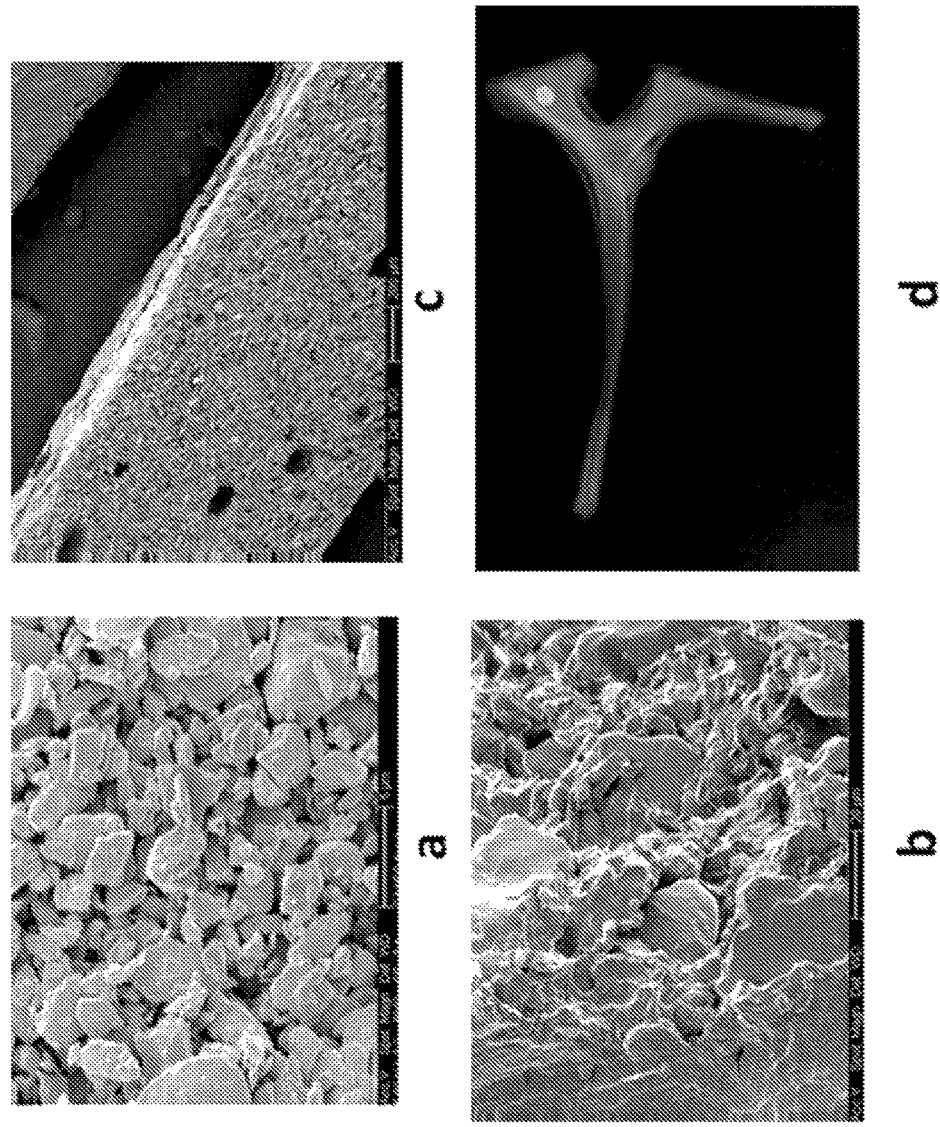
FIG. 14a is a scanning electron microscope (SEM) micrograph of 1-pentene-capped bismuth particles (5-μm scale bar)
FIGS. 14b-14c are SEM micrographs of the 1-pentene-capped bismuth particles dispersed in silicone (200-μm, and 20-μm scale bars, respectively)
FIG. 14d is an X-ray of a T-bone from a beef steak with a silicone-impregnated bismuth marker placed on the bone.

FIG. 14*a* is a scanning electron microscope (SEM) photograph of the 1-pentene-capped bismuth particles. FIGS. 14*b*-14*c* are SEM micrographs of the 1-pentene-capped bismuth particles dispersed in silicone. FIG. 14*d* is an X-ray of a T-bone from a beef steak with a silicone bismuth marker placed on the bone.

Figure 15:
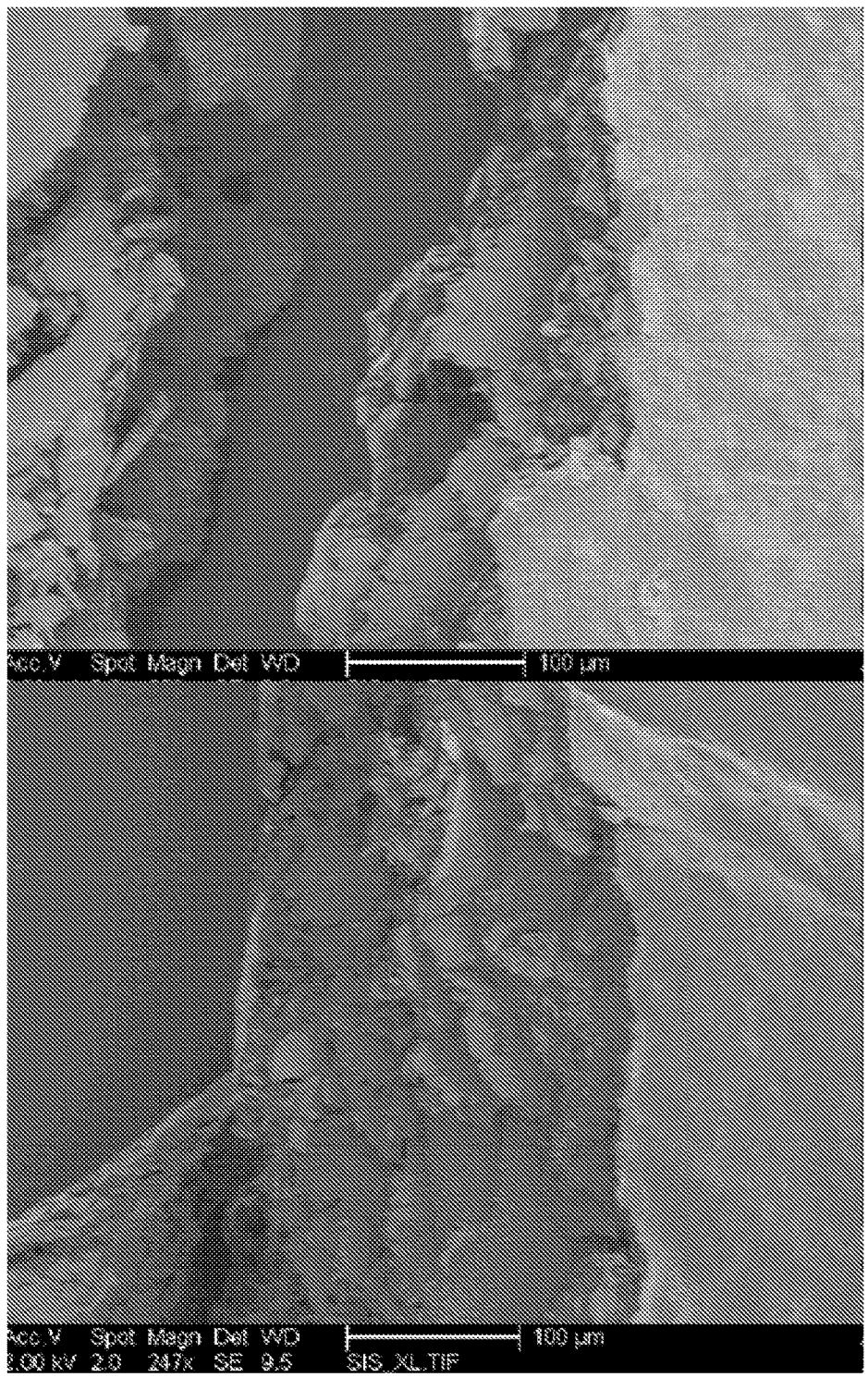
FIG. 15 is two SEM micrographs of styrene-capped bismuth particles dispersed in polystyrene. The scale bars in both images are 100 μm.

B. Styrene-Capped Bismuth Particles in Polystyrene and Polyurethane:

10 mL fresh styrene was milled with 5.7806 g bismuth for 20 minutes. The product was collected by centrifugation, washed in toluene, and dried into a powder for further use. 1.1668 g polystyrene and 4.3032 g bismuth with styrene surface capping were dissolved in toluene and molded in a watchglass. FIG. 15 is two SEM micrographs of styrene-capped bismuth particles dispersed in polystyrene.

Figure 16:
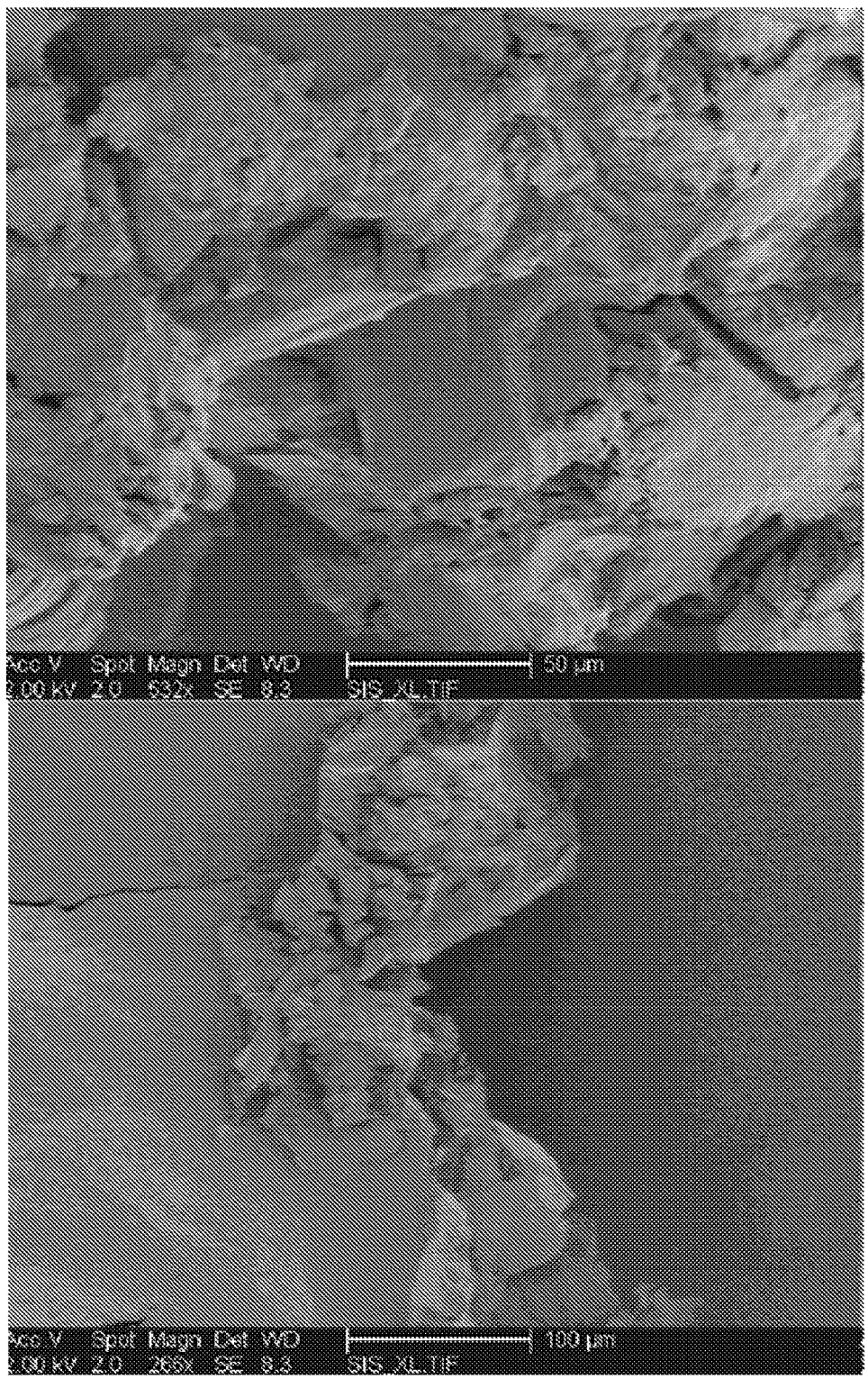
FIG. 16 is two SEM micrographs of styrene-capped bismuth particles dispersed in polyurethane. The scale bar in the top image is 50 μm; the scale bar in the bottom images is 100 μm.

C. Dihydroxyacetone-Capped Bismuth Particles in Polyurethane:

5.1433 g bismuth was milled with 5.13 g dihydroxyacetone. The powder was collected by centrifugation and washed with water. The suspension was then passed through a 74-μm sieve and dried to powder for further use. 1.6364 g dihydroxyacetone-capped bismuth particles (74-um sieved) was mixed with 0.3739 g methylene di-p-phenyl diisocyanate flakes in 20 mL chloroform. The mixture was stirred at 70° C. for 45 minutes. Next, 23.2973 g polyethylene glycol in 40 mL chloroform was added and the solution was stirred for 3 hours at 70° C. The solution was then poured into a watchglass to dry. FIG. 16 is two photographs of styrene-capped bismuth particles dispersed in polyurethane.

Figure 17:
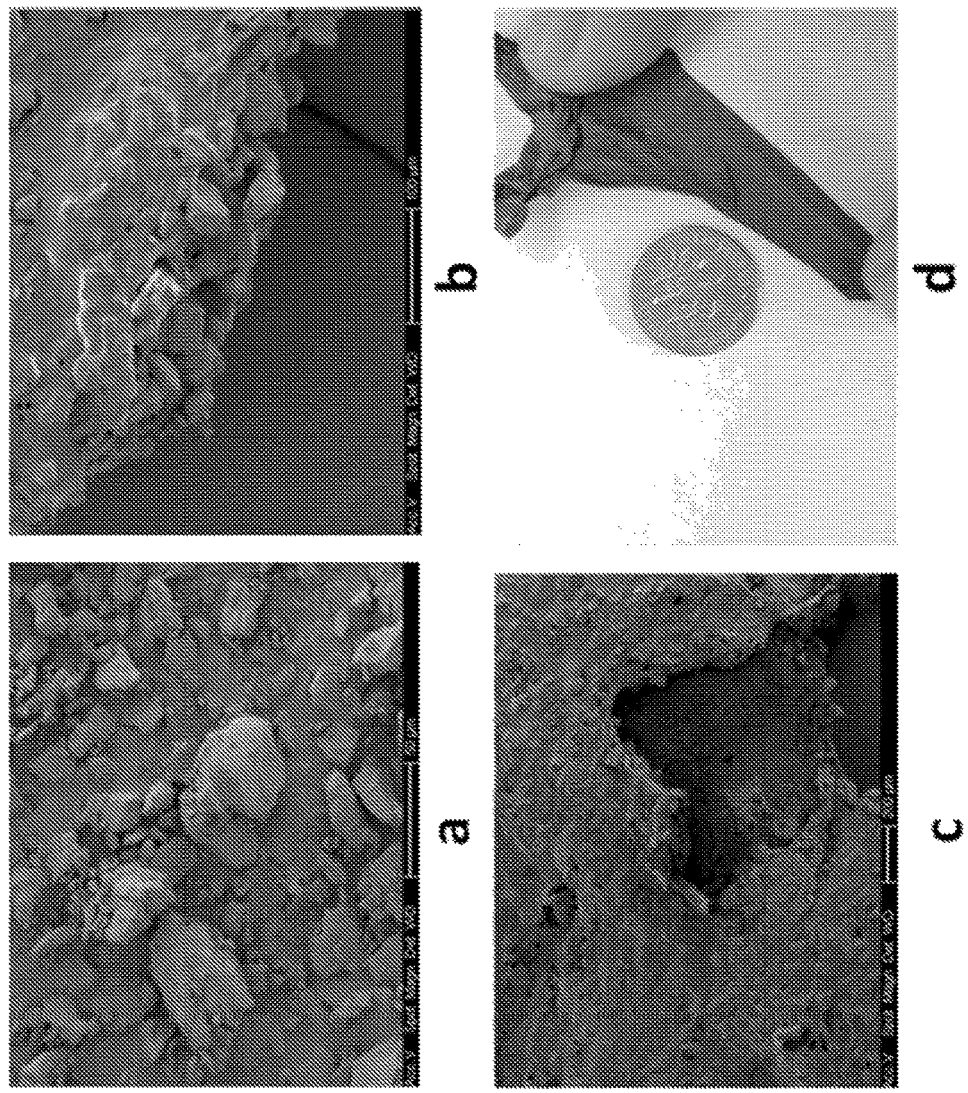
FIG. 17a is an SEM micrograph of dihydroxyacetone-capped bismuth particles (scale bar is 50 μm)
FIGS. 17b-17c are SEM micrographs of dihydroxyacetone-capped bismuth particles dispersed in latex and subsequently dried (scale bars are 100 μm and 200 μm, respectively)
FIG. 17d is a photograph of the latex comprising dihydroxyacetone-capped bismuth particles.

D. Dihydroxyacetone-Capped Bismuth Particles in Latex:

Dihydroxyacetone-capped bismuth particles were prepared as described above in part B. 2.1442 g dihydroxyacetone-capped particles (74 um sieved) was mixed with 1.48829 g liquid latex suspension, and dried in a watchglass. FIG. 17*a* is an SEM micrograph of dihydroxyacetone-capped bismuth particles. FIGS. 17*b*-*c* are SEM micrographs of the dihydroxyacetone-capped bismuth particles dispersed in latex. The bismuth-containing latex demonstrated acceptable structural elasticity (FIG. 17*d*).

Figure 18:
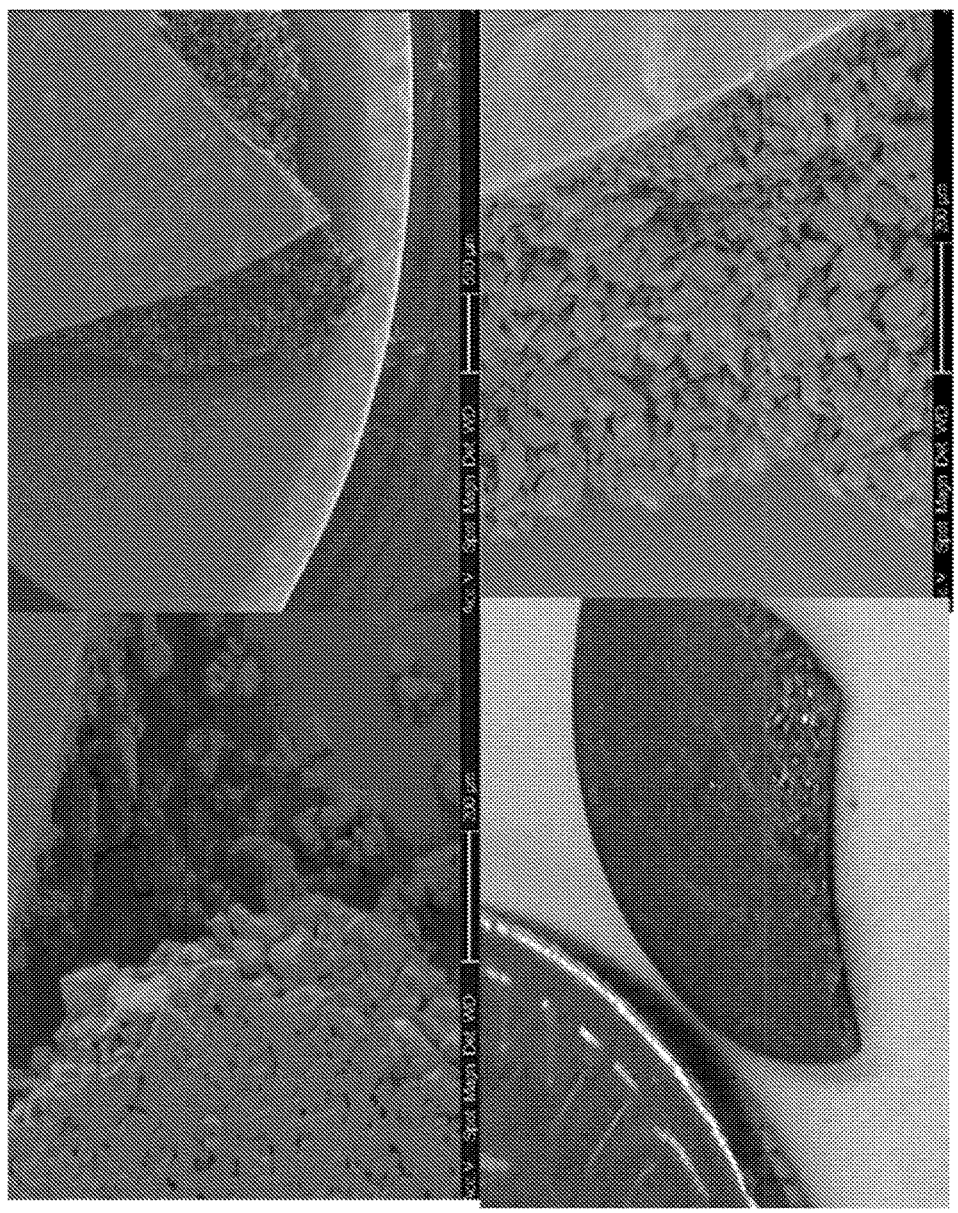
FIG. 18 is a series of SEM micrographs of dihydroxyacetone-capped bismuth particles dispersed in a dextran solution and subsequently dried. The scale bars in the top left and lower right images are 200 μm; the scale bar in the upper right image is 500 μm. The coin in the lower left image is a U.S. dime.

E. Dihydroxyacetone-Capped Bismuth Particles in Dextran Ink:

Dihydroxyacetone-capped bismuth particles were prepared as described above in part B. 1.1902 g dihydroxyacetone-capped bismuth (74 um sieved) was mixed in 800 μL water with 0.1137 g dextran (MW 86,000) and dried on paper, Parafilm® or glass. A sample dried on Parafilm® was removed and broken to expose bismuth particles embedded in the sugar matrix (FIG. 18).

Figure 19:
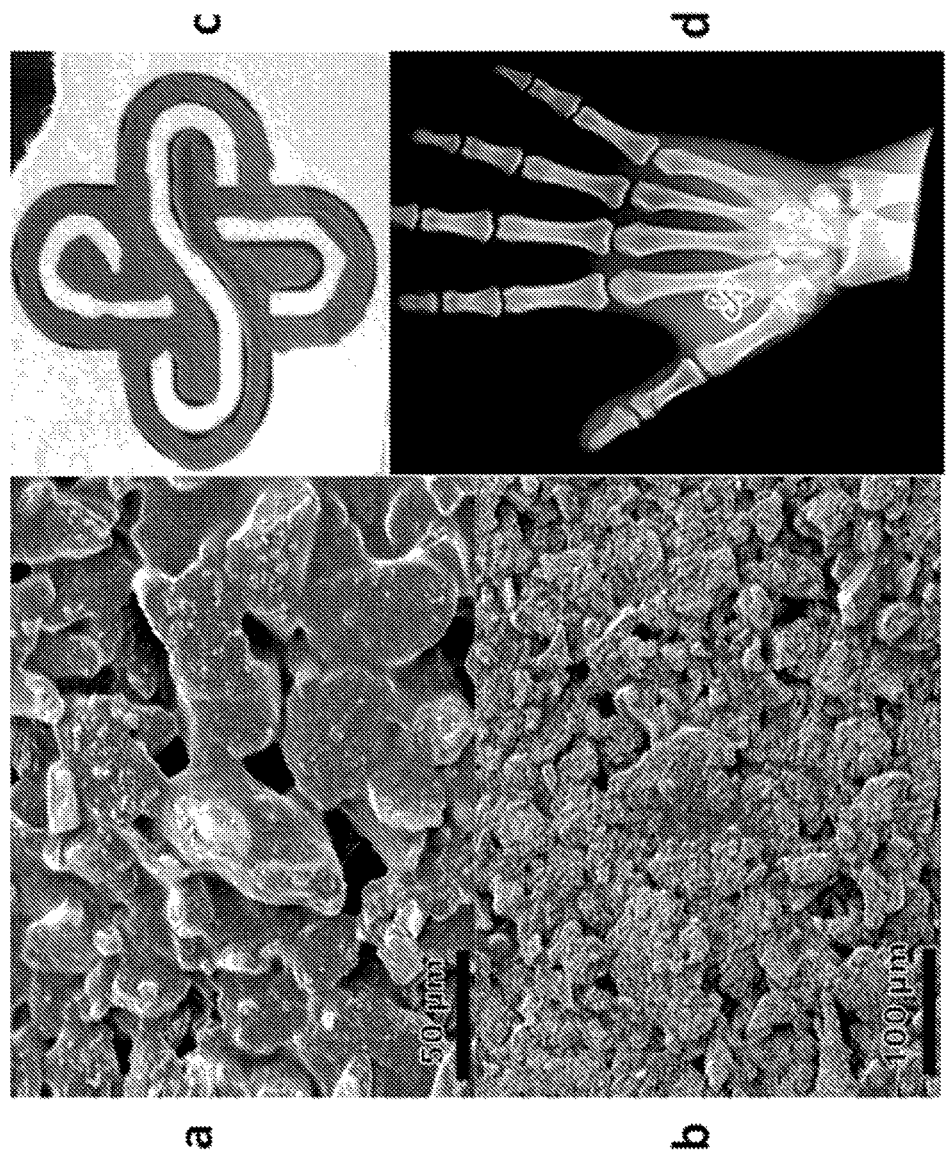
FIGS. 19a-b are SEM micrographs of styrene-capped bismuth particles dispersed in polystyrene ink and subsequently dried (scale bars are 50 μm and 100 μm, respectively.
FIG. 19c is a photograph of a logo drawn with the bismuth particle ink.
FIG. 19d is an X-ray of the logo placed underneath a hand phantom having a composition that simulates the density and X-ray opacity of human tissue.

F. Styrene-Capped Bismuth Particles in Polystyrene Ink:

3.3690 g styrene-capped bismuth particles were milled in 32 mL 0.5M polystyrene/toluene solution for 20 minutes. The product was centrifuged and washed in toluene, then dried to a hard solid product. The dry, solid product was dissolved in a minimal amount of toluene, and pipetted through a glass Pasteur pipette as an ink. FIGS. 19*a*-19*b* are SEM micrographs of the styrene-capped bismuth particles dispersed in polystyrene ink and subsequently dried. FIG. 19*c* is a photograph of a logo drawn with the ink. FIG. 19*d* is an X-ray of the logo placed on an X-ray compatible hand model.

Example 5

Coated Bismuth Particles Prepared by Bottom-Up Synthesis, and Compositions Including the Particles General Procedure:

Each synthesis included a bismuth salt, a solvent, a reducing agent, and a coating/capping agent. Suitable bismuth salts include $BiI_3$, $BiCl_3$, $BiBr_3$, $Bi(NO_3)_3 \cdot 5H_2O$, bismuth acetate, bismuth citrate, and bismuth oxide. Suitable solvents include water, ethylene glycol, propylene glycol, glycerol, pentanediol, polyethylene glycol 200, oleylamine, chloroform, hexanes, cyclohexane, toluene, styrene, tetrahydrofuran, dimethylformamide, decylamine, hexylamine. Suitable reducing agents include $NaBH_4$, borane morpholine, borane trimethyltetramine, triethylene tetramine, polyols (e.g., ethylene glycol, glycerol, propanediol, polyethylene glycol), oleylamine, hexylamine, decylamine. Suitable coating/capping agents include glucose, fructose, acetone, polyvinylpyrrolidone, oxaloacetic acid, dihydroxyacetone, dextran, maltose, mannose, and thiols.

A. Glucose-Capped Bismuth Particles in Polyurethane:

15.4144 g $Bi(NO_3)_3 \cdot 5H_2O$ and 31.5316 g glucose were mixed in 350 mL ethylene glycol and heated to approximately 80° C. Next, 7.0616 g borane trimethylamine was dissolved in 100 mL ethylene glycol and added to the nanoparticle solution. Particles were grown for 20 seconds at 90-95° C. before ice water was added. The particles were collected by centrifugation and washed with water.

Figure 20:
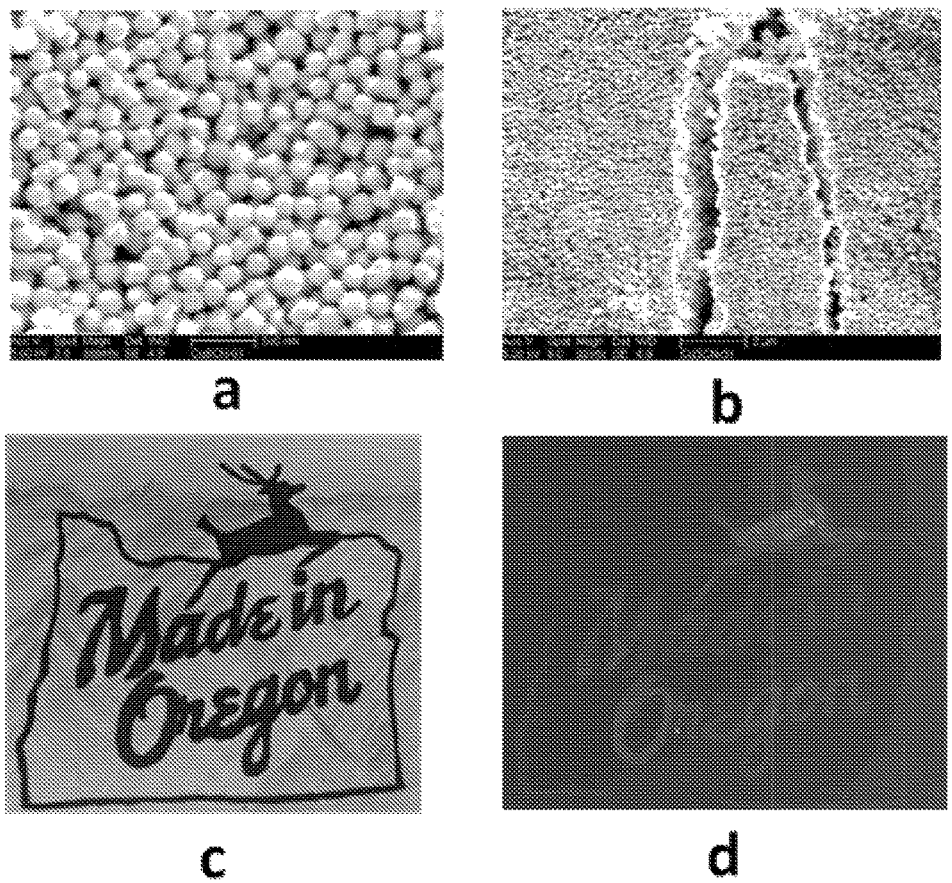
FIGS. 20a-20b are SEM micrographs of glucose-capped bismuth particles (scale bars are 500 nm and 2 μm, respectively)
FIG. 20c is a photograph of a logo drawn with the glucose-capped bismuth particle ink.
FIG. 20d is an X-ray of the logo.

B. Glucose-Capped Bismuth Particles in Water Ink:

Glucose-capped bismuth particles were prepared as described above in part A. The particles were dried to a powder and dissolved in a minimal amount of water to provide flowability of the particles. FIGS. 20*a*-20*b* are SEM micrographs of the glucose-capped bismuth particles. FIG. 20*c* is a photograph of a logo drawn with the glucose-capped bismuth particle ink. FIG. 20*d* is an X-ray of the logo.

Figure 21:
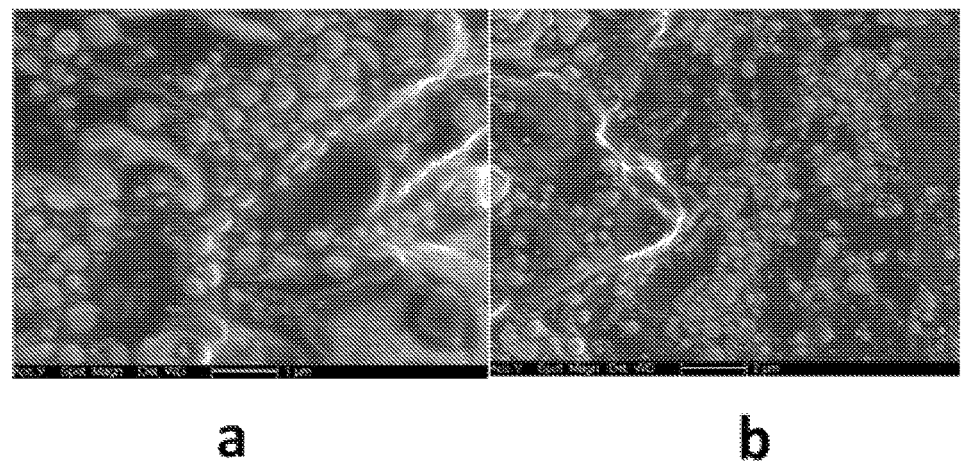
FIGS. 21a-21b are SEM micrographs of oleylamine-capped bismuth nanoparticles. The scale bar for the left image is 1 μm; the scale bar for the right image is 2 μm.

C. Oleylamine-Capped Bismuth Particles in Poly(Methyl Methacrylate) (PMMA):

Bismuth salt—$BiI_3$, solvent/reducing agent/surfactant—oleylamine. 0.9680 g $BiI_3$ and 40 mL oleylamine were heated to 210° C. for 2 hours and cooled with cyclohexane. The resulting particles were washed and collected by centrifugation in cyclohexane and then toluene, and dried for further use. FIGS. 21*a*-21*b* are SEM micrographs of the oleylamine-coated bismuth nanoparticles. The particles may be dispersed in PMMA.

Example 6

Radiopaque Plastics Including Organothiol-Coated Bismuth Particles

Bismuth is a chalcophile. Thus, bismuth microparticles and nanoparticles can interact/bond with sulfur groups. Accordingly, hydrophobic bismuth particles may be prepared by dispersing bismuth microparticles and/or nanoparticles into an aqueous solution comprising an organothiol, such as an alkyl thiol. The hydrophobic, thiol-coated particles may be extracted into a relatively non-polar solvent, which can be removed (e.g., by filtration and/or evaporation) to yield hydrophobic, thiol-coated bismuth particles. Ideally, solvent is completely removed. The nanoparticles may be introduced into plastic (e.g., polypropylene) by any suitable means, such as by adding the particles to molten plastic, adding the particles to plastic pellets and then melting the pellets, or by adding the particles to a solution comprising monomers and then polymerizing the monomers to form a plastic with embedded particles. A sufficient concentration of particles is added to the plastic to ensure radiopacity. The bismuth particle-containing plastic may be molded and/or machined by conventional means. The small size and hydrophobicity of the thiol-coated bismuth particles facilitates incorporation into plastics with minimal or no disruption of the polymeric matrix. A radiopaque plastic object may be prepared by incorporating the thiol-coated bismuth particles throughout the plastic object, or by incorporating a small piece of bismuth particle-containing plastic into a larger plastic object.

Embodiments of a radiopaque polymeric composition include a polymeric matrix, and a plurality of bismuth particles dispersed within the polymeric matrix, at least some of the bismuth particles comprising an elemental bismuth core and an outer coating comprising at least one hydrophobic, hydrophilic, or amphiphilic coating agent. In some embodiments, the at least one hydrophobic or amphiphilic coating agent is an alkane, an alkene, an aliphatic alcohol, an aliphatic amine, an aliphatic carboxylic acid, a carbohydrate, a phenyl-substituted alkene, a thiocarboxylate, polyacrylic acid, polyvinylpyrrolidone, or a combination thereof. In any or all of the above embodiments, the outer coating may be substantially continuous. In any or all of the above embodiments, the coating agent may adhere to the elemental bismuth core by chemical bonding, electrostatic interaction, or a combination thereof. In any or all of the above embodiments, the bismuth particles may be microparticles, nanoparticles, or a combination thereof.

Embodiments of a radiopaque surgical sponge include a radiopaque member comprising the radiopaque polymeric composition of any or all of the above embodiments. The polymeric matrix may be silicone, and the radiopaque member may be impregnated with or coated with the polymeric composition. In any or all of the above embodiments, the at least one hydrophobic, hydrophilic, or amphiphilic coating agent may be hexane, 1-pentene, oleic acid, or a combination thereof. In any or all of the above embodiments, at least a portion of the radiopaque member is attached securely to a surface of the sponge. In any or all of the above embodiments, the radiopaque member may be a cotton string or an acrylic fiber string.

Embodiments of a plastic object have at least a portion that includes the radiopaque polymeric composition of any or all of the above embodiments. The portion has a sufficient size and a sufficient concentration of bismuth particles to enable X-ray visualization of the plastic object. In some embodiments, substantially all of the plastic object comprises the radiopaque polymeric composition. In any or all of the above embodiments, the polymeric matrix may be polypropylene, poly(methylmethacrylate), polyethylene, poly(tetrafluoroethylene), polystyrene, polyethylene terephthalate, polyurethane, or a combination thereof.

Embodiments of a radiopaque ink include the radiopaque polymeric composition of any or all of the above embodiments. In some embodiments, the at least one hydrophobic or amphiphilic coating agent is a carbohydrate or a phenyl-substituted alkene.

Embodiments of a radiopaque tag include the radiopaque polymeric composition of any or all of the above embodiments. In one embodiment, the radiopaque tag consists essentially of the radiopaque polymeric composition. In another embodiment, the radiopaque polymeric composition is a coating on a tag substrate. In any or all of the above embodiments, the tag may further include an adhesive capable of forming a permanent bond or a temporary, removable bond to an object.

Embodiments of a radiopaque ink include a solvent and a plurality of bismuth particles dispersed in the solvent, at least some of the bismuth particles comprising an elemental bismuth core and an outer coating comprising at least one hydrophobic, hydrophilic, or amphiphilic coating agent. The at least one hydrophobic, hydrophilic, or amphiphilic coating agent may be an alkene, a carbohydrate, an alkanethiol, a thiocarboxylate, an aliphatic amine, polyacrylic acid, polyvinylpyrrolidone, or a combination thereof.

In one embodiment, radiopaque coated bismuth particles comprising an elemental bismuth core and an outer coating are made by combining bismuth and at least one coating agent to produce a mixture; subjecting the mixture to mechanical mixing comprising ball-milling, grinding, or a combination thereof, wherein the mechanical mixing is sufficient to break apart at least a portion of the bismuth to form bismuth microparticles, bismuth nanoparticles, or a combination thereof, whereby the at least one coating agent covalently binds, ionically binds, or adsorbs to outer surfaces of the bismuth microparticles, bismuth nanoparticles, or combination thereof to form coated bismuth particles; and isolating coated bismuth particles from the mixture. Coated bismuth particles may be isolated by extracting at least some of the coated bismuth particles from the mixture with a solvent, and recovering coated bismuth particles by removing the solvent. In any or all of the above embodiments, the at least one coating agent may be an alcohol, an alkane, an alkene, an alkylquinolinium cation, an amine, phenyl-substituted alkene, a carbohydrate, a carboxylic acid, a ketone, an aldehyde, a thiocarboxylic acid, an organothiol, a perhalogenated alkyl phosphonate, a perhalogenated alkyl siloxane, or a combination thereof. In some embodiments, the at least one coating agent is an aliphatic carboxylic acid, an aliphatic amine, an aliphatic alcohol, an aliphatic thiol, or a combination thereof.

In another embodiment, radiopaque coated bismuth particles comprising an elemental bismuth core and an outer coating are made by at least partially solubilizing a bismuth salt in a solution comprising a solvent and at least one coating agent to form a solubilized bismuth solution; adding a reducing agent to the solubilized bismuth solution to reduce bismuth ions and form elemental bismuth particles, whereby the at least one coating agent forms an outer coating on the elemental bismuth particles to form radiopaque coated bismuth particles comprising an elemental bismuth core and an outer coating comprising the coating agent; and isolating the radiopaque coated bismuth particles. In some embodiments, the at least one coating agent is an alcohol, an alkane, an alkene, an alkylquinolinium cation, an amine, phenyl-substituted alkene, a carbohydrate, a carboxylic acid, a ketone, an aldehyde, a thiocarboxylic acid, an organothiol, a perhalogenated alkyl phosphonate, a perhalogenated alkyl siloxane, or a combination thereof. In any or all of the above embodiments, the reducing agent may be sodium borohydride, triethylene tetramine, borane trimethyltetramine, borane morpholine, a polyol, an aliphatic amine, or a combination thereof. In any or all of the above embodiments, the bismuth salt may be bismuth nitrate pentahydrate, bismuth boride, bismuth chloride, bismuth iodide, bismuth acetate, bismuth citrate, bismuth oxide, or a combination thereof. In any or all of the above embodiments, isolating the radiopaque coated bismuth particles may include recovering the radiopaque coated bismuth particles from the solution via centrifugation, filtration, extraction into a non-polar solvent, precipitation, or a combination thereof. In any or all of the above embodiments, the at least one coating agent comprises a functional group capable of imparting a positive charge or a negative charge to the outer coating, or the at least one coating agent may be amphiphilic and the resulting radiopaque coated bismuth particles are hydrophobic.

In one embodiment, a radiopaque surgical sponge is made by preparing radiopaque coated bismuth particles according to any or all of the above embodiments, dispersing the radiopaque coated bismuth particles in a non-polar solvent to provide solvent-coated bismuth particles, impregnating or coating a member with the mixture, drying the impregnated or coated member, and incorporating the impregnated or coated member into a surgical sponge. In some embodiments, the non-polar solvent is hexane. In any or all of the above embodiments, the coating agent may be oleic acid. In any or all of the above embodiments, the mixture may have a bismuth:silicone mass ratio of 0.5 to 20. In any or all of the above embodiments, the member may be a cotton string or acrylic fiber string. In any or all of the above embodiments, incorporating the impregnated or coated member into the surgical sponge may include embedding the impregnated or coated member into the surgical sponge or securely attaching the impregnated or coated member to the surgical sponge.

In one embodiment, a radiopaque plastic object is made by preparing radiopaque coated bismuth particles according to any or all of the above embodiments, and incorporating the radiopaque coated bismuth particles into at least a portion of the plastic object. In some embodiments, incorporating the radiopaque coated bismuth particles into at least a portion of the plastic object includes combining the radiopaque coated bismuth particles with molten plastic, combining the radiopaque coated bismuth particles with plastic pellets and subsequently melting the plastic pellets, or combining the radiopaque coated bismuth particles with monomers and subsequently polymerizing the monomers to form a plastic. In any or all of the above embodiments, the radiopaque coated bismuth particles are incorporated into at least a portion of the plastic object. In any or all of the above embodiments, the radiopaque coated bismuth particles may be incorporated substantially throughout the plastic object.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A radiopaque polymeric composition, comprising:
   a polymeric matrix; and
   a plurality of bismuth particles dispersed within the polymeric matrix, the bismuth particles comprising an elemental bismuth core and an outer coating comprising at least one hydrophobic, hydrophilic, or amphiphilic coating agent, wherein the at least one hydrophobic, hydrophilic, or amphiphilic coating agent is a $C_1$-$C_{20}$ aliphatic compound, ROH, RSH, $RNH_2$, $R_2CO$, RCOOH, RC(S)OH, RC(S)SH, an alkylquinolinium cation, a phenyl-substituted alkene, a perhalogenated alkyl phosphonate, styrene, or a combination thereof, where R is a $C_1$-$C_{20}$ alkyl group or a $C_2$-$C_{20}$ alkenyl group and where the $C_1$-$C_{20}$ aliphatic compound is an alkane, an alkene, or an alkyne.

2. The radiopaque polymeric composition of claim 1, wherein the polymeric matrix is silicone, latex, polypropylene, poly(methylmethacrylate), polyethylene, poly(tetrafluoroethylene), polystyrene, polyethylene terephthalate, polyurethane, or a combination thereof.

3. The radiopaque polymeric composition of claim 1, wherein the at least one hydrophobic, hydrophilic, or amphiphilic coating agent is hexane, 1-pentene, oleic acid, acetone, 1-decene, ethanol, ethanolamine, octanol, octylamine, oleylamine, oxaloacetic acid, styrene, a perfluorinated alkyl phosphonate, or a combination thereof.

4. A method for making the radiopaque polymeric composition of claim 1, the method comprising:
   at least partially solubilizing a bismuth salt in a solution comprising a solvent and at least one hydrophobic, hydrophilic, or amphiphilic coating agent to form a solubilized bismuth solution, wherein the at least one hydrophobic, hydrophilic, or amphiphilic coating agent is a $C_1$-$C_{20}$ aliphatic compound, ROH, RSH, $RNH_2$, $R_2CO$, RCOOH, RC(S)OH, RC(S)SH, an alkylquinolinium cation, a phenyl-substituted alkene, a a perhalogenated alkyl phosphonate, styrene, or a combination thereof, where R is a $C_1$-$C_{20}$ alkyl group or a $C_2$-$C_{20}$ alkenyl group and where the $C_1$-$C_{20}$ aliphatic compound is an alkane, an alkene, or an alkyne;
   adding a reducing agent to the solubilized bismuth solution to reduce bismuth ions and form elemental bismuth particles, whereby the at least one hydrophobic, hydrophilic, or amphiphilic coating agent forms an outer coating on the elemental bismuth particles to form radiopaque coated bismuth particles comprising an elemental bismuth core and an outer coating comprising the coating agent;
   isolating the radiopaque coated bismuth particles; and
   dispersing the radiopaque coated bismuth particles in a polymeric matrix by
     (i) combining the radiopaque coated bismuth particles in a non-polar solvent to provide solvent-coated bismuth particles, dispersing the solvent-coated bismuth particles in unpolymerized silicone to form a bismuth/silicone mixture, impregnating or coating a member with the mixture, whereby the unpolymerized silicone polymerizes to form a radiopaque polymeric composition, the radiopaque polymeric composition comprising a polymeric matrix and a plurality of bismuth particles dispersed within the polymeric matrix,
     (ii) combining the radiopaque coated bismuth particles with molten plastic,
     (iii) combining the radiopaque coated bismuth particles with plastic pellets and subsequently melting the plastic pellets, or
     (iv) combining the radiopaque coated bismuth particles with monomers and subsequently polymerizing the monomers to form a plastic.

5. The method of claim 4, wherein the coating agent is hexane, 1-pentene, oleic acid, acetone, 1-decene, ethanol, ethanolamine, octanol, octylamine, oleylamine, oxaloacetic acid, styrene, a perfluorinated alkyl phosphonate, or a combination thereof.

6. The radiopaque polymeric composition of claim 1, wherein the bismuth particles are microparticles, nanoparticles, or a combination thereof.

7. The method of claim 4, wherein the bismuth salt is bismuth nitrate pentahydrate, bismuth boride, bismuth chloride, bismuth iodide, bismuth acetate, bismuth citrate, bismuth oxide, or a combination thereof.

8. The method of claim 4, wherein isolating the radiopaque coated bismuth particles comprises recovering the radiopaque coated bismuth particles from the solution via centrifugation, filtration, extraction into a non-polar solvent, precipitation, or a combination thereof.

9. A method for making the radiopaque polymeric composition of claim 1, the method comprising:

combining elemental bismuth and at least one hydrophobic, hydrophilic, or amphiphilic coating agent to produce a mixture, wherein the at least one hydrophobic, hydrophilic, or amphiphilic coating agent is a $C_1$-$C_{20}$ aliphatic compound, ROH, RSH, $RNH_2$, RCOOH, styrene, or a combination thereof, where R is a $C_1$-$C_{20}$ alkyl group or a $C_2$-$C_{20}$ alkenyl group, and where the $C_1$-$C_{20}$ aliphatic compound is an alkane, an alkene, or an alkyne;

subjecting the mixture to mechanical mixing comprising ball-milling, grinding, or a combination thereof, wherein the mechanical mixing is sufficient to break apart at least a portion of the elemental bismuth to form bismuth microparticles, bismuth nanoparticles, or a combination thereof, whereby the at least one hydrophobic, hydrophilic, or amphiphilic coating agent covalently binds, ionically binds, or adsorbs to outer surfaces of the bismuth microparticles, bismuth nanoparticles, or combination thereof to form coated bismuth particles;

isolating coated bismuth particles from the mixture; and dispersing the coated bismuth particles in a polymeric matrix by
  (i) combining the coated bismuth particles in a nonpolar solvent to provide solvent-coated bismuth particles, dispersing the solvent-coated bismuth particles in unpolymerized silicone to form a bismuth/silicone mixture, impregnating or coating a member with the mixture, whereby the unpolymerized silicone polymerizes to form a radiopaque polymeric composition, the radiopaque polymeric composition comprising a polymeric matrix and a plurality of bismuth particles dispersed within the polymeric matrix,
  (ii) combining the coated bismuth particles with molten plastic,
  (iii) combining the coated bismuth particles with plastic pellets and subsequently melting the plastic pellets, or
  (iv) combining the coated bismuth particles with monomers and subsequently polymerizing the monomers to form a plastic.

10. The method of claim 9, wherein the coating agent is hexane, 1-pentene, oleic acid, 1-decane, 1-decene, styrene, or a combination thereof.

11. The method of claim 9, wherein isolating coated bismuth particles from the mixture further comprises:
  extracting at least some of the coated bismuth particles from the mixture with a solvent; and
  recovering coated bismuth particles by removing the solvent.

* * * * *